United States Patent [19]

Tatsuta et al.

[11] Patent Number: 5,705,650
[45] Date of Patent: Jan. 6, 1998

US005705650A

[54] PROCESS FOR PREPARING 1,2,4-THIADIAZOLE DERIVATIVES

[75] Inventors: Kuniaki Tatsuta, Tokyo-to; Yasuyuki Kurita, Osaka-fu; Takashi Inagaki, Osaka-fu; Ryonosuke Yoshida, Osaka-fu, all of Japan

[73] Assignee: Katayama Seiyakusyo Co., Ltd., Osaka, Japan

[21] Appl. No.: 657,170

[22] Filed: Jun. 3, 1996

Related U.S. Application Data

[62] Division of Ser. No. 225,920, Apr. 11, 1994, Pat. No. 5,585,494, which is a continuation of Ser. No. 941,246, Sep. 4, 1992, abandoned.

[30] Foreign Application Priority Data

| Sep. 12, 1991 | [JP] | Japan | 3-233056 |
| Sep. 12, 1991 | [JP] | Japan | 3-233104 |
| Jan. 28, 1992 | [JP] | Japan | 4-012821 |

[51] Int. Cl.$^6$ .................................................. C07D 285/08
[52] U.S. Cl. ...................................................... 548/128
[58] Field of Search ........................................... 548/128

[56] References Cited

U.S. PATENT DOCUMENTS

4,567,275  1/1986  Teraji et al. .......................... 548/128

FOREIGN PATENT DOCUMENTS

| 60114/80 | 1/1981 | Australia . |
| 22245 | 1/1981 | European Pat. Off. . |
| 27599 | 4/1981 | European Pat. Off. . |
| 231475 | 8/1987 | European Pat. Off. . |
| 959191 | 2/1957 | Germany . |
| 62309546 | 11/1988 | Japan . |
| 2-28170 | 1/1990 | Japan . |

OTHER PUBLICATIONS

Vivona, N., et al, Journal of the Chemical Society Perkin I, 1616–1619 (1986).
Macaluso, G., et al, Heterocycles, vol. 24, No. 12, 3433–3439 (1986).
March, Advanced Organic Chemistry, 629–631 (1985).
Macaluso, G., et al, Chemical Abstracts 107:77714w (1987).
Zayed, E., et al, Chemical Abstracts 98:143312n (1983).
Zayed, E., et al., Arch. Pharm. (Weinheim, Ger.) 316(2), 105–110 (1983).
Goerdeler, J., et al, Chemical Abstracts 53:8166f (1959).
Sridevi, G., et al, Chemical Abstracts 111:7293s (1989).
Goto, J., et al, The Journal of Antibiotics, 36, 557–571 (1984).
Csendes, I. et al, The Journal of Antibiotics, 36, 1020–1033 (1983).

*Primary Examiner*—Robert Gerstl

[57] ABSTRACT

An improved process for the production of 5-amino-1,2,4-thiadiazol-3-yl-(2-(lower)-alkoxyimino)acetic acids starting from 5-substituted- or unsubstituted-3-aminoisoxazole compounds is disclosed herein. The title compounds are useful as acylating agents for the production of 7-acylaminocephalosporins.

1 Claim, No Drawings

PROCESS FOR PREPARING 1,2,4-THIADIAZOLE DERIVATIVES

This is a divisional of application Ser. No. 08/225,920 filed on Apr. 11, 1994, U.S. Pat. No. 5,585,494, which is a continuation of application Ser. No. 07/941,246, filed Sep. 4, 1992, now abandoned.

BACKGROUND OF THE INVENTION

1. Field of the Invention

The present invention relates to 1,2,4-thiadiazole compounds as well as the production and a use thereof. Particularly, the present invention relates to 1,2,4-thiadiazole compounds utilizable as the starting materials for the synthesis of acylating agents which are used in the production of 7-acylaminocephalosporins useful as antibiotics as well as a process for their production and a use of them.

2. Background Information

Various 7-acylaminocephalosporins have been known as antibiotics and various processes for the production of them have also been reported. Among these processes, most typical one is a process in which 7-aminocephalosporins are converted into 7-acylaminocephalosporins by the action of an acylating agent. A wide variety of acylating agents are proposed for use in this converting process, because antimicrobial activity of the produced 7-acylaminocephalosporins greatly depends on the acylating agents. Among the acylating agents, 2-(5-amino-1,2,4-thiadiazol-3-yl)acetic acid and its reactive derivatives are widely applied due to the fact that the produced 7-[2-(5-amino-1,2,4-thiadiazol-3-yl)acetamido]cephalosporins generally have excellent antimicrobial activity.

Although various methods have been known for the production of the above 2-(5-amino-1,2,4-thiadiazol-3-yl) acetic acid and its reactive derivatives, all these methods have any drawbacks from the viewpoint of commercial production. For example, it is reported that said acid can be produced by protecting amino group of 5-amino-3-methyl-1,2,4-thiadizole, reacting the product with lithium diisopropylamide prepared from diisopropylamine and butyl lithium, and converting methyl group to carboxymethyl group by introducing carbon dioxide, but this method has a fault that butyl lithium should be used at a temperature as low as −78° C. for preparing lithium diisopropylamide.

The present inventors discovered, in the course of research for the development of commercially advantageous process for the production of 2-(5-amino-1,2,4-thiadiazol-3-yl)acetic acid and its reactive derivatives, a novel rearrangement reaction in which isoxazole compounds are converted into 1,2,4-thiadiazole compounds, said rearrangement reaction leading to a new and commercially advantageous preparation method, comprising a series of reaction steps, for the production of 2-(5-amino-1,2,4-thiadiazol-3-yl)acetic acid and its reactive derivatives. The present invention provides a step of producing lower alkyl 2-(5-substituted-amino-1,2,4-thiadiazol-3-yl)acetate by the rearrangement of 3-amino-5-lower alkoxy isoxazole, said step being the key step in the series of steps for the production. The present invention also provides a step of producing lower alkyl 2-(5-substituted-amino-1,2,4-thiadiazol-3-yl)-2-oxoacetate in a commercially advantageous manner by oxidizing lower alkyl 2-(5-substituted-amino-1,2,4-thiadiazol-3-yl)acetate. The present invention further provides a process for the production of 2-(5-amino-1,2,4-thiadiazol-3-yl)acetic acid and its reactive derivative which comprises a series of steps including said key step.

SUMMARY OF THE INVENTION

The present invention provides the following processes and products.

(1) A process for the production of 5-amino-1,2,4-thiadiazol-3-yl-(2-(lower)alkoxyimino)acetic acid compound which comprises a) reacting an isoxazole of the formula:

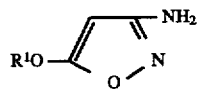

wherein $R^1$ is lower alkyl, with either a thiocyanate and an acyl halide or a reaction product of them to give a 1,2,4-thiadiazolylacetic acid compound of the formula:

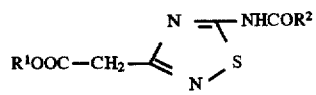

wherein $R^1$ is as defined above, and
$R^2$ is optionally substituted lower alkyl, optionally substituted phenyl, optionally substituted phenyl (lower) alkyl, optionally substituted lower alkoxy, optionally substituted phenoxy or optionally substituted-phenyl(lower)alkyloxy, or b) i) reacting 3-aminoisoxazole with either a thiocyanate and an acyl halide or a reaction product of them to give an isoxazolylthiourea of the formula:

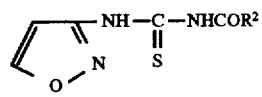

wherein $R^2$ is defined above, ii) subjecting the compound (III) to rearrangement reaction to give a 1,2,4-thiadiazolylacetaldehyde of the formula:

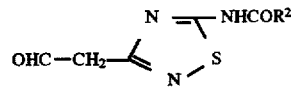

wherein $R^2$ is as defined above, or acetal or hemiacetal thereof, iii) oxidizing the compound (IV) obtained in (ii) to give a 1,2,4-thiadiazolylacetic acid of the formula:

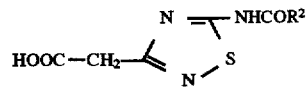

wherein $R^2$ is as defined above, and iv) esterifying the compound (V) to give lower alkyl 1,2,4-thiadiazolylacetate of the formula (II), or c) i) oxidizing the compound of the formula (II) with dimethyl sulfoxide, iodine and sulfuric acid to give a 1,2,4-thiadiazolyl-(2-oxo)acetate compound of the formula:

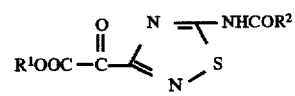

wherein $R^1$ and $R^2$ are as defined above, ii) reacting the compound (VI) with an N-(lower) alkoxyamine to give a 1,2,4-thiadiazolyl-(2-(lower) alkoxyimino)acetate compound of the formula:

$$\underset{R^1OOC-C}{\overset{R^3O-N}{\underset{\parallel}{}}}\underset{N}{\overset{N}{\diagdown}}\underset{S}{\overset{}{\diagup}}NHCOR^2 \qquad VII$$

wherein $R^1$ and $R^2$ are as defined above, and $R^3$ is lower alkyl, halo(lower)alkyl, carboxy(lower)alkyl or (lower)alkoxycarbonyl(lower)alkyl, and iii) optionally hydrolyzing the compound (VII) to give a 1,2,4-thiadiazolyl-(2-(lower)alkoxyimino)acetic acid compound of the formula:

$$\underset{HOOC-C}{\overset{R^3O-N}{\underset{\parallel}{}}}\underset{N}{\overset{N}{\diagdown}}\underset{S}{\overset{}{\diagup}}NR^2 \qquad VIII$$

wherein $R^2$ and $R^3$ are as defined above, or d) i) reacting a syn-isomer of 1,2,4-thiadiazolacetic acid compound of the formula:

$$R^4OOC-CH_2-\underset{N}{\overset{N}{\diagdown}}\underset{S}{\overset{}{\diagup}}NHR^5 \qquad IX$$

wherein $R^4$ is carboxy-protecting group and
$R^5$ is amino-protecting group, with a nitrous acid ester to give a syn-isomer of 1,2,4-thiadiazol-(2-hydroxyimino)acetic acid compound of the formula:

$$\underset{R^4OOC-C}{\overset{HO-N}{\underset{\parallel}{}}}\underset{N}{\overset{N}{\diagdown}}\underset{S}{\overset{}{\diagup}}NHR^5 \qquad X$$

wherein $R^4$ and $R^5$ are as defined above,
ii) reacting the compound (X) with
iia) a compound of the formula:

$$R^3-X \qquad (XI)$$

wherein $R^3$ is lower alkyl, halo(lower)alkyl, carboxy (lower)alkyl or (lower)alkoxycarbonyl(lower)alkyl, and X is halogen atom, in the presence of silver oxide, or
iib) a compound of the formula:

$$R^3-Y \qquad (XII)$$

wherein $R^3$ is as defined above and Y is acid residue, in the presence of barium oxide and barium hydroxide, to give a syn-isomer of 1,2,4-thiadiazolyl-(2-substituted-oxyimino)acetic acid compound of the formula:

$$\underset{R^4OOC-C}{\overset{R^3O-N}{\underset{\parallel}{}}}\underset{N}{\overset{N}{\diagdown}}\underset{S}{\overset{}{\diagup}}NHR^5 \qquad XIII$$

wherein $R^3$, $R^4$ and $R^5$ are as defined above, and optionally subjecting the compound (XIII) to elimination reaction of protecting group(s).

(2) A process for the production of 1,2,4-thiadiazolylacetic acid compound which comprises reacting an isoxazole of the formula:

$$R^1O-\underset{O}{\overset{}{\diagdown}}\underset{N}{\overset{}{\diagup}}NH_2 \qquad I$$

wherein $R^1$ is lower alkyl, with either a thiocyanate and an acyl halide or a reaction product of them to give a 1,2,4-thiadiazolylacetic acid compound of the formula:

$$R^1OOC-CH_2-\underset{N}{\overset{N}{\diagdown}}\underset{S}{\overset{}{\diagup}}NHCOR^2 \qquad II$$

wherein $R^1$ is lower alkyl, and
$R^2$ is optionally substituted lower alkyl, optionally substituted phenyl or optionally substituted phenyl(lower) alkyl, optionally substituted lower alkoxy, optionally substituted phenoxy or optionally substituted phenyl (lower)alkoxy.

(3) A process for the production of 1,2,4-thiadiazol-3-yl-(2-oxo)-acetic acid compound which comprises oxidizing the compound of the formula (II):

$$R^1OOC-CH_2-\underset{N}{\overset{N}{\diagdown}}\underset{S}{\overset{}{\diagup}}NHCOR^2 \qquad II$$

wherein $R^1$ is lower alkyl, and
$R^2$ is optionally substituted lower alkyl, optionally substituted phenyl or optionally substituted phenyl(lower) alkyl, optionally substituted lower alkoxy, optionally substituted phenoxy or optionally substituted phenyl (lower)alkyloxy, with dimethyl sulfoxide, iodine and sulfuric acid to give a 1,2,4-thiadiazolyl-(2-oxo)acetate compound of the formula:

$$\underset{R^1OOC-C}{\overset{O}{\underset{\parallel}{}}}\underset{N}{\overset{N}{\diagdown}}\underset{S}{\overset{}{\diagup}}NHCOR^2 \qquad VI$$

wherein $R^1$ and $R^2$ are as defined above.

(4) A process for the production of 5-amino-1,2,4-thiadiazol-3-yl-(2-(lower)alkoxyimino)acetic acid compound which comprises i) reacting an isoxazole of the formula:

$$R^1O-\underset{O}{\overset{}{\diagdown}}\underset{N}{\overset{}{\diagup}}NH_2 \qquad I$$

wherein $R^1$ is lower alkyl, with a thiocyanate and a haloformate or a reaction product of them to give a 1,2,4-thiadiazolylacetic acid compound of the formula:

$$R^1OOC-CH_2-\underset{N}{\overset{N}{\diagdown}}\underset{S}{\overset{}{\diagup}}NHCOR^2 \qquad II$$

wherein $R^1$ is lower alkyl, and
$R^2$ is optionally substituted lower alkyl, optionally substituted phenyl or optionally substituted phenyl (lower) alkyl, optionally substituted lower alkoxy, optionally substituted phenoxy or optionally substituted phenyl(lower)alkyloxy, and ii) oxidizing the compound of the formula (II) to give a 1,2,4-thiadiazolyl-(2-oxo)acetate compound of the formula:

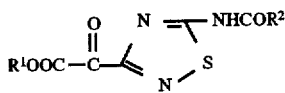   VI wherein R¹ and R² are as defined above, iii) reacting the compound (VI) with an N-(lower) alkoxyamine to give a 1,2,4-thiadiazolyl-(2-(lower)alkoxyimino)acetate compound of the formula:

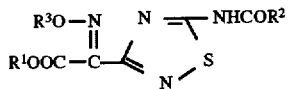   VII wherein R¹ and R² are as defined above, and R³ is lower alkyl, halo(lower)alkyl, carboxy(lower)alkyl or (lower)alkoxycarbonyl(lower)alkyl, and iv) optionally hydrolyzing the compound (VII) to give a 1,2,4-thiadiazolyl-(2-(lower)alkoxyimino)acetic acid compound of the formula:

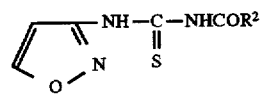   VIII wherein R³ are as defined above.

(5) A process for the production of 1,2,4-thiadiazolylacetic acid compound which comprises reacting 3-aminoisoxazole with either a thiocyanate and an acyl halide or a reaction product of them to give an isoxazolylthiourea of the formula:

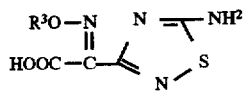   III wherein R² is optionally substituted lower alkyl, optionally substituted phenyl or optionally substituted phenyl(lower)alkyl, optionally substituted lower alkoxy, optionally substituted phenoxy or optionally substituted phenyl(lower)alkyloxy, ii) subjecting the compound (III) to rearrangement reaction to give a 1,2,4-thiadiazolylacetaldehyde of the formula:

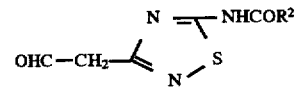   IV wherein R² is as defined above, or acetal or hemiacetal thereof, iii) oxidizing the compound (IV) obtained in (ii) to give a 1,2,4-thiadiazolylacetic acid of the formula:

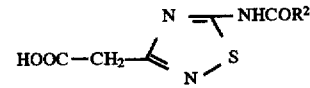   V wherein R² is as defined above, and iv) optionally esterifying the compound (V) to give lower alkyl 1,2,4-thiadiazolylacetate of the formula (II).

(6) An isoxazolylthiourea of the formula:

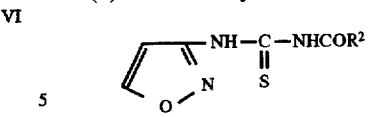   III wherein R² is optionally substituted lower alkyl, optionally substituted phenyl or optionally substituted phenyl(lower)alkyl, optionally substituted lower alkoxy, optionally substituted phenoxy or optionally substituted phenyl(lower)alkyloxy.

(7) A 1,2,4-thiadiazolylacetaldehyde of the formula:

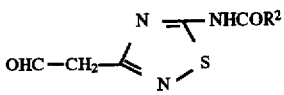   IV wherein R² is optionally substituted lower alkyl, optionally substituted phenyl or optionally substituted phenyl(lower)alkyl, optionally substituted lower alkoxy, optionally substituted phenoxy or optionally substituted phenyl(lower)alkyloxy.

(8) A process for the production of 5-amino-1,2,4-thiadiazol-3-yl-(2-(lower)alkoxyimino)acetic acid compound which comprises i) reacting a syn-isomer of the compound (X) of the formula:

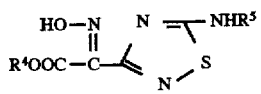   X wherein R⁴ is carboxy-protecting group and R⁵ is amino-protecting group, with iia) a compound of the formula:

   XI wherein R³ is lower alkyl, halo(lower)alkyl, carboxy(lower)alkyl or (lower)alkoxycarbonyl(lower)alkyl, and X is halogen atom, in the presence of silver oxide, or iib) a compound of the formula:

   XII wherein R³ is as defined above and Y is acid residue, in the presence of barium oxide and barium hydroxide, to give a syn-isomer of 1,2,4-thiadiazol-(2-substituted-oxyimino)acetic acid compound of the formula:

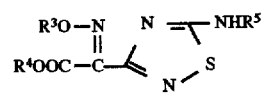   XIII wherein R³ R⁴ and R⁵ are as defined above and optionally subjecting the compound (XIII) to elimination reaction of protecting group(s) to give an 5-amino-1,2,4-thiadiazol-3-yl-(2-(lower)alkoxyimino)acetic acid compound of the formula:

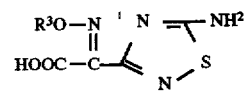   VIII wherein R³ is as defined above.

(9) A process for the production of 5-amino-1,2,4-thiadiazol-3-yl-(2-hydroxyimino)acetic acid compound which comprises reacting a 1,2,4-thiadiazolacetic acid compound of the formula:

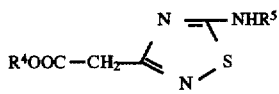     IX wherein $R^4$ is a carboxy-protecting group and
$R^5$ is amino-protecting group, with a nitrous acid ester to give a 1,2,4-thiadiazol-(2-hydroxyimino)acetic acid compound of the formula:

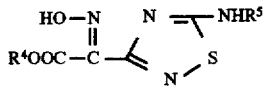     X wherein $R^4$ and $R^5$ are as defined above.

DETAILED DESCRIPTION OF THE INVENTION

The terms and definitions described in this specification are illustrated as follows:

Only for the convenient sake, the partial structure of the formula:

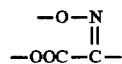

includes both of the geometric structures "syn" and "anti" unless otherwise specified. The "syn"-isomer as described in this specification is intended to mean the isomer having the geometric structure in which —o— bonded to N and —COO— bonded to C are on the same side in relation to the C=N double bond, regardless to the above definition of the partial structure.

The thiadiazolyl group is well known to lie in tautomeric relation with a thiadiazolinyl group. Accordingly, it is to be understood that both of the said groups are substantially the same, and the tautomers consisting of such groups are regarded as the same compounds especially in the manufacturing chemistry. Therefore, both of the tautomeric forms of the compounds having such groups in their molecule are included in the scope of this invention and designated inclusively with one expression "thiadiazolyl" only for the convenient sake throughout this specification.

The term "lower" is intended to include a group having 1 to 6 carbon atoms unless otherwise specified.

Therefore, the term "lower alkyl" as a group or a moiety of phenyl(lower)alkyl, carboxy(lower)alkyl or halo(lower)alkyl include saturated and straight or branched chain hydrocarbon radicals containing 1 to 6, preferably 1 to 5 and more preferable 1 to 4 carbon atoms, such as methyl, ethyl, propyl, isopropyl, butyl, t-butyl, pentyl, hexyl.

The term "phenyl(lower)alkyl" includes, for example, benzyl phenethyl, etc.

The word "substituted" means that any group can be present on lower alkyl, phenyl, phenyl(lower) alkyl, lower alkyloxy, phenyloxy and pheny(lower)alkyloxy groups, and such a group may be any one that does not have adverse effect on the reaction of the present invention, and chosen from lower alkyl, lower alkoxy, hydroxy, halogen and nitro.

The term "halo(lower)alkyl" refers to a lower alkyl group as defined above which is substituted with at least one and preferably 1 to 3 halogen atoms and includes for example, chloromethyl, bromomethyl, fluoromethyl, trifluoromethyl, 1,2-dichloromethyl, 1,2,2-trichloromethyl, chloroporpyl, chlorobutyl, chloropentyl, chlorohexyl etc.

The term "carboxy(lower)alkyl" refers to a lower alkyl as defined above which is substituted with at least one carboxy group, such as carboxymethyl, 1-carboxyethyl, 2-carboxyethyl and 1-methyl-1-carboxyethyl.

The term "lower alkoxycarbonyl" is represented by the formula: R—O—CO—R'— wherein R is a lower alkyl defined above and R' is a lower alkylene obtainable by removing a hydrogen atom from the lower alkyl group as defined above.

The term "optionally" means that the subsequently described event or circumstance may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution.

The term "halogen" includes chlorine, bromine, iodine and fluorine.

The term "carboxy-protecting group" and "amino-protecting group" have the meanings used in peptide synthesis.

The typical carboxy protecting groups together with the eliminating method thereof are described, for example, in "Shinjikkenkagakukoza" 14, 2535-2544 and Peptide Synthesis (Second Edition, M. Bodansky. Y. S. Klausner and M. A. Ondetti, John Wily & Sons, 1976), Chapter 4, and there are included, for example, lower alkyl, such as methyl (removable by acid or alkali), ethyl (the same as methyl) and t-butyl (removable by HCl/$CH_2Cl_2$, $CH_3COOH$, TsOH/ACOH, etc), halo(lower)alkyl, such as 2,2,2-trichloroethyl (removable by Zn/AcOH and HCOOH, etc), loweralkylthio (lower)alkyl, such as methylthioethyl (removable by $CH_3I$ and then alkali), lower alkoxy(lower)alkyl, such as methoxymethyl (removable by acid), arylsulfonyl(lower)alkyl, such as tosylethyl (removable by NaOH/dioxane), optionally substituted arylthio(lower)alkyl, such as p-nitrophenylthio (removable by alkali after oxydizing to a sulfone), aryl(lower)alkyl, such as benzyl (removable by $H_2$/Pd, Na/$NH_3$, NaOH/dioxane, HBr/AcOH, etc), p-methoxybenzyl (removable by $H_2$/Pd, $CF_3COOH$, HCOOH, etc), 2,4,6-trimethoxybenzyl (removable by HBr/AcOH), pentamethlbenzyl (removable by $CF_3COOH$), p-nitrobenzyl (removable by $H_2$/Pd, NaOH), benzhydryl (removable by $H_2$/Pd, NaOH), trityl (removable by NaOH, HCl/$CH_3OH$), anthranylmethyl (removable by HBr/AcOH, NaOH, $CF_3COOH$) and hydroxamic acid (removable by $HIO_4$).

The typical amino-protecting groups together with the eliminating method thereof is described, for example, in "Shinjikkenkagakukoza" 14, 2555-2569 and "Peptide Synthesis" (The Second Edition, M. Bodansky. Y. S. Klausner and M. A. Ondetti, John Wily & Sons, 1976), Chapter 4, there are included, for example; as a acyl type, lower alkanoyl, such as formyl (removable by HCl/$CH_3OH$), acetyl (removable by acid or alkali), halo(lower)alkanoyl, such as 2-chloropropionyl (removable by acid or alkali), arylcarbonyl, such as benzoyl (removable by acid or alkali), aryl(lower)alkanoyl, such as phenylpropionyl (removable by acid or alkali); as a urethane type, lower alkoxycarbonyl, such as methoxycarbonyl, ethoxycarbonyl, t-buthoxycarbonyl (removable by HBr or HCl/AcOH), aryl (lower)alkoxycarbonyl, such as benzyloxycarbonyl (removable by $H_2$/Pd, HI or HBr/AcOH, etc), 2-(p-biphenyl) isopropoxycarbonyl (removable by AcOH/HCOOH, trifluoroacetic acid, etc); as a aralkyl type, aryl(lower)aralkyl, such as benzyl (removable by $H_2$/Pd, Na/$NH_3$), trityl (removable by $H_2$/Pd); and as an azomethine type, aryl(lower)alkylidene, such as benzylidene (removable by $H_2$/Pd, HCl).

In the above mentioned groups, "aryl" group includes a group having one to three bezene rings.

Since "carboxy-protecting group" or "amino-protecting group" defined above is finally to be eliminated, selection of the group is not important.

The term "acid residue" includes sulfur acid such as sulfuric acid, organosulfonic acid (e.g. lower alkyl sulfonic acid, such as methane sulfonic acid, ethane sulfonic acid and aryl sulfonic acid, such as benzene sulfonic acid, toluene sulfonic acid), and organocarboxylic acid, such as tartaric acid.

The above series of the process steps from an isoxazole compound (I) to a 1,2,4-thiadiazol-3-yl-(2-(lower) alkoxyimino)acetic acid of the formula (VIII), via 1,2,4-thiadiazol-3-yl acetic acid are illustrated below in order.

In the first step of the present invention, isoxazol (I) is reacted with a thiocyanate and acyl halide or reaction product of them to give a 1,2,4-thiadiazolylacetic acid compound (II).

The starting substance, i.e. isoxazole can be prepared by reacting, -dialkoxyacrylonitrile with hydroxylamine as described in Japanese Patent Publication B No. 45-39702.

Thiocyanate as the reacting reagent is preferably alkaline metal thiocyanate (e.g. sodium thiocyanate, potassium thiocyanate), and an acyl halide is preferably a compound of the formula: $R^2COX$ wherein $R^2$ is as defined above and X is a halogen atom, specifically, lower alkyl haloformate, phenylhaloformate, phenyl(lower)alkyl haloformate, phenylalkyl carbonyl halide, benzoyl halide and phenyl(lower) alkylcarbonyl halide which may be substituted. Isoxazole may be reacted with thiocyanate and acyl halide, however usually thiocyanate is previously reacted with acyl halide to prepare acylisothiocyanate, which, after separation or without separation, which is advantageously reacted with isoxazole. The reaction with thiocyanate and acyl halide or the reaction with acylisothiocyanate is preferably carried out in a inert solvent, particularly in a polar solvent, such as acetonitrile, dimethylformamide, tetrahydrofuran, etc.

The term "reaction product" includes not only the direct products produced by the reaction of thiocyanate and acyl halide but also the compounds having the same structure but produced by the reaction of other compounds. Normally, the products have the structure of acylisothiocyanate.

The typical process is illustrated below: methyl chloroformate is reacted with potassium thiocyanate by heating in acetonitrile, followed by cooling and then 3-amino-methoxy isooxazole is added thereto to react at room temperature. The reaction mixture is poured onto ice water to give the precipitates of methyl 2-(5-methoxycarbonylamino-1,2,4-thiadiazol-3-yl)acetate, which are separated. In the case where the product is not crystallized such as methyl 2-(5-benzyloxycarbonylamino-1,2,4-thiadiazol-3-yl)acetate, this is extracted with a solvent such as ethyl acetate in order to separate. If necessary, it is possible to purify by sillica gel chromatography.

As the typical compounds of a 1,2,4-thiadiazolyl acetic acid compound (II), there may be mentioned 2-(5-methoxycarbonylamino-1,2,4-thiadiazol-3-yl)acetic acid, 2-(5-ethoxycarbonylamino-1,2,4-thiadiazol-3-yl)acetic acid, methyl 2-(5-ethoxycarbonylamino-1,2,4-thiadiazol-3-yl)acetate, methyl 2-(5-phenoxycarbonylamino-1,2,4-thiadiazol-3-yl)acetate, methyl 2-(5-benzyloxycarbonylamino-1,2,4-thiadiazol-3-yl)acetate, methyl 2-(5-phenylcarbonylamino-1,2,4-thiadiazol-3-yl)acetate, ethyl 2-(5-phenylcarbonylamino-1,2,4-thiadiazol-3-yl)acetate, methyl 2-(5-t-butylcarbonylamino-1,2,4-thiadiazol-3-yl)acetate and ethyl 2-(5-(4-nitrobenzoyl)carbonylamino-1,2,4-thiadiazol-3-yl)acetate.

In the second step, the obtained 1,2,4-thiadiazolylacetic acid compound (II) is oxidized to give 1,2,4-thiadiazolyl-2-oxo-acetic acid compound (VI).

The oxidation is carried according to a known method, for example, using selenium dioxide, which is not adapted in a industrial scale production because of its high toxicity. As the result of the intensive study of various oxidizing agent, it has been found that oxidation reaction is advantageously effected using dimethyl sulfoxide, iodine and sulfuric acid which does not have the toxicity such as that of selenium dioxide. Therefore, dimethyl sulfoxide, iodine and sulfuric acid are particularly preferred as the oxidizing agent. The amounts of these oxidizing agents are 3–30 equivalent weight, preferably 5–15 equivalent of dimenthyl sulfoxide, 0.05–10 equivalent of iodine, preferably 0.1 equivalent, and 0.05–1 equivalent of sulfuric acid, preferably 0.1 equivalent with respect to 1,2,4-thiadiazolyl acetic acid (II), respectively. The oxidation reaction is smoothly carried out under heating at 80°–100° C. The reaction solvent is not necessarily used, but when used, it may be chosen from ethyl acetate, benzene, toluene and acetone.

In the third step, 1,2,4-thiadiazolyl-2-oxoacetic acid (IV) is reacted with a lower alkoxy amine to give 1,2,4-thiadiazolyl-2-(lower)alkoximino acetic acid (VII).

The lower alkoxy amine is represented by the formula: $R^3ONH_2$ wherein $R^3$ is as defined above, and the typical examples are methoxyamine, ethoxyamine, propoxyamine, etc. In general, the reaction is advantageously carried out at the temperature of 5°–40° C. On the reaction, the presence of an acid substance, such as hydrochloric acid is preferred as a catalyst. The reaction solvent is not necessarily used, but when used, it may be appropriately chosen from methanol, ethanol, etc.

In the fourth step, ester moiety is eliminated from the acetic ester group at the position 3 on 1,2,4-thiadiazol-3-yl-2-(lower)alkoxyimino)acetate (VII), or the substituted carbonyl group is eliminated from the substituted carbonylamino group at the position 5. These eliminations are effected by heating in the presence of a basic substance (such as sodium hydroxide). In general, as a temperature, 30°–100° C. is usually preferred. If the kind of the basic substance or the heating temperature is appropriately chosen, the both eliminations of ester moiety at the position 3 and substituted carbonyl moiety at the position 5 can be effected simultaneously or succesively to give 5-amino-1,2, 4-thiadiazol-3-yl-(2-(lower)alkoxyimino)acetic acid compound (VIII). The elimination is usually carried out in an aqueous medium.

It has now been found that the compound (VII) is hydrolized in good yield to the compound (VIII) via 5-acylamino-1,2,4-thiadiazol-3-yl-(2-(lower)alkoxyimino) acetic acid compound of the formula (XIV):

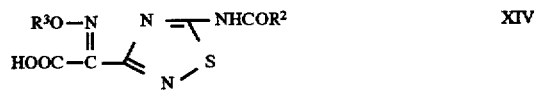

wherein $R^2$ is lower alkoxy or optionally substituted alkyl or optionally substituted aryl. The present process comprises hydolyzing the acetic ester group of the compound (VII) wherein $R^2$ is optionally substituted alkyl or optionally substituted phenyl with alkali such as alkali metal hydroxides (for example, NaOH, KOH, etc) to obtain the compound (XIV) and then hydrolyzing it to the compound (VIII) with aqueous ammonia or organic amines, for example, primary amine such as methylamine, ethylamine, butyl amine, cyclohexylamine, etc or secondary amine, such as dimethylamine, diethanolamine, etc.

The reaction products in the above described steps optionally may be separated and further purified, or may be applied as such to a next step without purification. The compound (VIII) may be used as an acylating agent for the production of 7-acylaminosephalosporins according to conventional methods.

The alternative process from 3-aminoisoxazole to 1,2,4-thiadiazolyl acetaldehyde (IV) or acetal or hemiacetal thereof is described below.

In the first step, 3-aminoisoxazole is reacted with a thiocyanate and acyl halide or reaction product of them to give an isoxazolylthiourea (III), which is subjected to rearrangement reaction to give 1,2,4-thiadiazolyl acetaldehyde (IV) or acetal or hemiacetal thereof.

The starting substance, i.e. 3-aminoisoxazole can be prepared by a known method which, for example, is described in Japanese Patent Publication A No. 59-128378 which comprises reacting 2-alkoxyacrylonitrile with hydroxylamine, and 3-aminoisoxazole is also available commercially and relatively at a low price.

The step from 3-aminoisoxazole to isoxazolylthiourea (III) is carried as described in the above mentioned step, for example, methyl chloroformate and potassium thiocyanate is reacted at 40° C.–80° C. for 0.5–6 hours in acetonitrile, followed by cooling and 3-aminoisoxazole (I) is added thereto. The resultant mixture is kept at 0°–10° C. for 0.5–4 hours in order to complete the reaction. The reaction mixture is poured onto ice water to give 1-(isoxazol-3-yl)-3-methoxycarbonylthiourea, which is filtered off. If the reaction product is not easily crystallized, it may be extracted by a solvent such as ethyl acetate. The product may be applied as such to the next step without separation.

In the second step, isoxazolylthiourea (III) is subjected to rearrangement reaction to give a 1,2,4-thiadiazolylacetaldehyde, acetal or hemiacetal thereof. This reaction is effected by heating at a temperature of which may be usually 20°–100° C., and optionally in the presence of an inert solvent such as methanol, ethanol, ethyl acetate, etc.

For example, 1-(isoxazol-3-yl)-3-methoxycarbonylthiourea is heated in methanol at 20°–60° C. for 0.5–4 hours to give precipitates, 2-(3-methoxycarbonylamino-1,2,4-thiadiazol-3-yl)acetaldehyde (IV) or acetal or hemiacetal, which is filtered off.

As described above, since the rearrangement reaction in the first step is easily effected only by heating, when the temperature of heating is appropriately chosen in the second step, the reactions of the both steps can be at least partially effected successively to give a mixture of isoxazolylthiourea (III) and thiadiazolylacetaldehyde (IV).

In the third step, thiadiazolylacetaldehyde (IV) is oxidized to give thiadiazolylacetic acid (V). The oxidization is effected by using an oxidizing reagent, such as silver oxide, chromate, permanganate, hydrogen peroxide, peracid, etc. especially peracetic acid. On the oxidation reaction, it is preferred to use an inert solvent, as a typical example, such as water, t-butanol, methylene chloride, acetic acid, etc. The reaction temperature is usually between 20°–60° C.

For example, 2-(5-methoxycarbonylamino-1,2,4-thiadiazol-3-yl)acetaldehyde is dissolved into a mixture of t-butanol and water, and 39% solution of peracid in acetic acid was added in dropwise thereto, then the resultant mixture is reacted overnight at a room temperature. After decomposition of excess peracid, the precipitated formed is filtered off to give 2-(5-methoxycarbonylamino-1,2,4-thiadiazol-3-yl)acetic acid.

Thiadiazolylacetic acid (V) according to the present invention is esterified by a conventional method and oxidized to convert the corresponding 1,2,4-thiadiazol-3-yl-2-oxoacetic acid ester (VI), then which is reacted with N-(lower)alkoxyamine to give the corresponding 1,2,4-thiadiazol-3-yl-2-(lower)alkoxyiminoacetic acid ester (VII). The obtained compound is optionally hydrolized to give 1,2,4-thiadiazol-3-yl-2-(lower)alkoxyimino-acetic acid (VIII) which is useful for a acylating reagent of the production of 7-acyl aminosepharosporin.

Further alternative process from syn-isomer of 1,2,4-thiadiazolylacetic acid compound (IX) to 1,2,4-thiadiazol-3-yl-(2-(lower)alkoxyimino)acetic acid compound (VIII) is described below.

In the first step, a syn-isomer of 1,2,4-thiadiazolylacetic acid compound (IX) is reacted with a nitrous acid ester to give a syn-isomer of 1,2,4-thiadiazolyl-(2-hydroxyimino) acetic acid compound (X).

Some of the starting substances, i.e. the compound (IX) can be prepared by the process as described in the Journal of Antibiotics, 36, 1020–1033, and the others can also be prepared in a similar process. The compounds (IX) can also be obtained by new method developed by the inventor of this invention, wherein lower alkoxyisoxazole is reacted with a thiocyanate and a haloformate.

As "nitrous acid ester", any ester can be used, but in view of availability and economy, lower alkoxy nitrite, such as methyl nitrite, ethyl nitrite, butyl nitrite are usually used. Since the ester group is eliminated, kind of the group is not important.

This reaction is effected in the presence of a catalyst. As the catalyst, an acid such as hydrochloric acid, sulfuric acid, etc or a salt such as lithium chloride are used. The amount of the catalyst is usually 0.1–2 equivalent weight, preferably 0.1–0.2 equivalent. The reaction is carried out in a solvent, such as tetrahydrofuran, ether, dimethylformamide, methanol, ethanol, buthanol, etc. The reaction proceeds at a room temperature, and is promoted by heating. The reaction product is in the form of a syn-isomer and can be separated by a conventional method in which, for example, the reaction solution is washed, concentrated to give the compound (X).

In the second step, a syn-isomer of the compound (X) is reacted with (a) $R^3$—X (XI) in the presence of silver oxide or (b) R—Y (XII) in the presence of barium oxide and barium hydroxide to give 1,2,4-thiadiazol-(2-substituted oxyimino)acetic acid compound (XIII), optionally from which amino-protecting group and/or carboxy protecting group are eliminated.

As the compound (XI), methyl iodide, ethyl iodide, ethyl bromoacetate, ethyl 2-methyl-2-bromopropionate, chloromethylfluoride, etc and dimethyl sulfate, diethyl sulfate may be used.

The reaction using the-compound (XI) or (XII) is effected in a solvent, such as chloroform, acetone, etc and well at a room temperature. While the alkylation in the presence of a basic catalyst is known, according to the present inventors, it has been now founded that the alkylation of the compound (X) by the combinations of potassium carbonate and the compound (XI), calcium oxide and the compound (XI), calcium oxide or calcium hydroxyde and the compound (XII), a mixture of calcium oxide and calcium hydroxide, barium oxide and the compound (XII), barium hydroxide and the compound (XII) give always (E)-isomer and only the alkylation by the combination of the present invention gives (Z)-isomer. The elimination reaction of the protecting group is carried out, for example, by the method described above for the protecting groups, under the conditions which are employed for the elimination of the protecting groups in the peptide synthesis. The protecting groups of $R^4$ and $R^5$ may be eliminated separately or simultaneously or successively. The reaction temperature is usually about room temperature. In the present reaction, starting from the compound (XIII) wherein $R^3$ is lower alkoxy carbonyl(lower) alkyl, there may be obtained the compound (V) wherein $R^3$ carboxy(lower)alkyl, and such a process is also included in the scope of the present invention.

The obtained compound (VIII) can be separated by a conventional method, for example, in which the reaction product is washed, extracted, concentrated, and optionally purified by recrystallization or silica gel chromatography to give the compound (VIII). The compounds obtained by the present invention are useful for a acylating reagent for the production of 7-acylaminosephalosporin antibiotics.

The following non-limiting examples illustrate the preparation of the compounds according to the present invention.

REFERENCE EXAMPLE 1

To a solution of malononitrile (12.0 g; 182 mmol) and methanol (7.35 ml; 182 mmol) in anhydrous ether (240 ml) was bubbled hydrogen chloride gas (8.5 g; 0.23 mol) over 1 hour under stirring at −5° C. After the reaction mixture was stirred at the same temperature for 1 hour and then at room temperature for 6 hours, white crystals formed were filtered off, washed with ether (100 ml×3) and dried under reduced pressure to give methyl cyanoacetimidate hydrochloride (23.8 g; yield 97.3%).

A suspension of methyl cyanoacetimidate hydrochloride (23.8 g; 177 mmol) in methanol (177 ml) was stirred at room temperature for 12 hours and then the reaction mixture was directly concentrated. The obtained residue was diluted by ethyl acetate (100 ml), washed with saturated sodium bicarbonate solution and saturated aqueous sodium chloride solution, dried over sodium sulfate and then concentrated. The crude syrup obtained was purified by distillation under reduced pressure to give 3,3,3-trimethoxypropanenitrile (bp:110°–112° C./19 mmHg:22.1 g; yield 86.0%).

NMR $\delta$(CDCl$_3$): 2.87(2H,s,CH$_3$), 3.36(9H,s,CH$_3$×3)

3,3,3-Trimethoxypropanenitrile (22.1 g; 153 mmol) was stirred at 222°–225° C. for 7 minutes. This reaction mixture was purified by distillation under reduced pressure to give 3,3-dimethoxyacrylonitrile (bp:112° C.−115° C./19 mmHg:13.6 g; yield 3 step 66.1%).

NMR $\delta$(CDCl$_3$): 3.50(1H,s,H-2), 3.74(3H,s,CH$_3$) 3.80 (3H,s,CH$_3$)

(B) To a solution of hydroxylamine hydrochloride (1.55 g, 22.3 mmol) in water (3.41 ml) was added 8N aqueous sodium hydroxide solution (3.35 ml; 26.8 mmol) under stirring at room temperature. The temperature was elevated to 45° C. and a solution of 3,3-dimethoxyacrylonitrile (2.27 g; 20.1 mmol) in methanol (5.50 ml) was added dropwise for 30 minutes and then the mixture was stirred at the same temperature for 1 hour. After disappear of 3,3-dimethoxyacrylonitrile was apparent, 8N sodium hydroxide (1.25 ml; 10.1 mmol) was added to the mixture at the same temperature and the temperature was elevated to 60° C. The mixture was stirred for 6 hours. After the reaction was completed, the reaction mixture was directly concentrated (60° C./19 mmHg: until an inorganic compound was begun to precipitate). The obtained concentrate was extracted with ethyl acetate (5 ml×3) and the extract was dried over sodium sulfate and concentrated and the residue was dried under reduced pressure to give 3-amino-5-methoxyisoxazole (1.63 g; yield 70.6%) as white crystals.

m.p. 82°–83° C. (hexane-ethyl acetate)

NMR $\delta$(CDCl$_3$): 3.93(5H,bs,CH$_3$+NH$_2$), 4.81(1H,s,H-4)

NMR $\delta$(CDCl$_3$+D$_2$O): 3.93 (3H,s,CH$_3$), 4.83(1H,s,H-4)

IR(CHL$_3$)cm$^{-1}$: 3840, 1628, 1487.

Anal. Calcd. for C$_4$H$_6$N$_2$O$_2$: C,42.11; H,5.30; N, 24.55 (%). Found: C,41.74; H, 5.06; N, 24.35(%).

EXAMPLE 1

A suspension of methyl chloroformate (167 μl; 2.16 mmol) and potassium thiocyanate (227 mg; 2.34 mmol) in acetonitrile (1.80 ml) was stirred at 70° C. for 30 minutes, and then 3-amino-5-methoxyisoxazole (205 mg; 1.80 mmol) was added to the suspension under stirring and ice-cooling. After stirring for 10 minutes at the same temperature and then for 15 minutes at room temperature, the reaction mixture was poured into ice-water (18 ml). The precipitates formed were filtered off, washed with water, then with ether and dried under reduced pressure to give methyl 2-(5-methoxycarbonylamino-1,2,4-thiadiazol-3-yl)acetate (334 mg, yield 80.6%).

m.p. 167°–169° C.(MeOH)

NMR $\delta$(CDCl$_3$): 3.73 (3H. s. COOCH$_3$) 3.95 (3H. s. NHCOOCH$_3$) 3.97 (2H. s. CH$_2$) 10.50(1H. bs. NH)

IR (CHCL$_3$)cm$^{-1}$: 3406. 1736. 1549.

Anal. Calcd. for C$_7$H$_9$N$_3$O$_4$S: C,36.36;H,3.92;N,18.17 (%). Found: C,36.40;H,3.94;N,18.11(%).

EXAMPLE 2

A suspension of ethyl chloroformate (124 μl; 1.29 mmol) and potassium thiocyanate (136 mg; 1.40 mmol) in acetonitrile (1.08 ml) was treated with 3-amino-5-methoxyisoxazole (123 mg; 1.08 mmol) in the same manner as in Example 1 except that ethyl chloroformate was substituted for methyl chloroformate to give methyl 2-(5-ethoxycarbonylamino-1,2,4-thiadiazol-3-yl)acetate (209 mg; yield 78.9%).

m.p. 110°–112° C.(MeOH)

NMR $\delta$(CDCl$_3$): 1.38(3H.t.CH$_3$) 3.73(3H.s.COOCH$_3$) 3.97(2H.s.CH$_2$COOCH$_3$) 4.39(2H.q.CH$_2$) 10.45(1H.bs.NH)

IR(CHCl$_3$)cm$^{-1}$: 3406, 1732, 1564.

Anal. Calcd. for C$_8$H$_{11}$N$_3$O$_4$S: C,39.18;H,4.52;N,17.13 (%). Found: C,39.16;H,4.40;N,17.18(%).

EXAMPLE 3

A suspension of phenyl chloroformate (232 μl; 1.85 mmol) and potassium thiocyanate (195 mg; 2.00 mmol) in acetonitrile (1.54 ml) was treated with 3-amino-5-methoxyisoxazole (170 mg; 1.49 mmol) in the same manner as in Example 1 except that phenyl chloroformate was substituted for methyl chloroformate to give methyl 2-(5-phenoxycarbonylamino-1,2,4-thiadiazol-3-yl)acetate (251 mg; yield 57.4%).

m.p. 162°–164° C.(MeOH)

NMR $\delta$(CDCl$_3$): 3.66(3H.s.CH$_3$) 3.99(2H.s.CH$_2$) 7.13–7.48(5H.m.ph) 10.87(1H.bs.NH)

IR(CHCl$_3$)cm$^{-1}$: 3432, 1743, 1576.

Anal. Calcd. for C$_{12}$H$_{11}$N$_3$O$_4$S C,49.14;H,3.78;N,14.33 (%). Found: C,48.81;H,3.79;N,14.31(%).

EXAMPLE 4

A suspension of benzyloxycarbonyl chloride (285 μl; 2.00 mmol) and potassium thiocyanate (210 mg; 2.17 mmol) in acetonitrile (1.67 ml) was treated with 3-amino-5-methoxyisoxazole (190 mg; 1.67 mmol) in the same manner as in Example 1. Since no crystallization was occurred when the reaction mixture was poured into ice-water, the mixture was extracted with ethyl acetate and the extract was purified by silica gel column chromatography to give methyl 2-(5-benzyloxycarbonylamino-1,2,4-thiadiazol-3-yl) acetate (128 mg; yield 24.9%).

m.p. 121°–123° C. (MeOH)

NMR δ(CDCl$_3$): 3.70(3H.s.CH$_3$) 3.85(2H.s.CH$_2$) 5.33 (2H.s.CH$_2$Ph) 7.35–7.45(5H.m.Ph) 9.96(1H.bs.NH)

IR(CHCl$_3$)cm$^{-1}$: 3404, 1736, 1564.

Anal. Calcd. for C$_{13}$H$_{13}$N$_3$O$_4$S: C,50.81;H,4.26;N,13.67 (%). Found: C,50.85;H,4.27;N,13.43(%).

In the same manner as described above, the following 1,2,4-thiadiazole compounds (I) were obtained.

Ethyl 2-(5-ethoxycarbonylamino-1,2,4-thiadiazol-3-yl) acetate, m.p. 102°–104.5° C.;

Ethyl 2-(5-methoxycarbonylamino-1,2,4-thiadiazol-3-yl) acetate, m.p. 158°–160° C.;

Ethyl 2-(5-benzyloxycarbonylamino-1,2,4-thiadiazol-3-yl)acetate, m.p. 89°–91° C.;

Ethyl 2-(5-isobutoxycarbonylamino-1,2,4-thiadiazol-3-yl)acetate, m.p. 64°–66° C.;

Ethyl 2-(5-n-hexyloxycarbonylamino-1,2,4-thiadiazol-3-yl)acetate, m.p. 70°–72° C.

EXAMPLE 5

A solution of methyl 2-(5-methoxycarbonylamino-1,2,4-thiadiazol-3-yl)acetate (48.0 mg; 2.08×10$^{-1}$ mmol), dimethyl sulfoxide (74.0 μl; 1.04 mmol), iodine (5.3 mg; 2.1× 10$^{-2}$ mmol) and concentrated sulfuric acid (0.6 μl) in ethyl acetate (480 μl) was stirred under heating with reflux for 3 hours (at the bath temperature of 100° C.).

The reaction mixture was allowed to cool and then diluted with ethyl acetate (1.0 ml), washed with saturated aqueous sodium sulfate solution, saturated aqueous sodium bicarbonate and saturated aqueous sodium chloride, dried over sodium sulfate, and then concentrated to give methyl 2-oxo-2-(5-methoxycarbonylamino-1,2,4-thiadiazol-3-yl)acetate (31.0 mg; yield 60.8%) as a foam.

m.p. 112°–117° C.

NMR δ(CDCl$_3$): 3.96(3H.s.CH$_3$), 4.02(3H.s.CH$_3$), 10.15 (1H.bs.NH)

IR(CHCl$_3$)cm$^{-1}$: 3406, 1759, 1546.

EXAMPLE 6

A solution of methyl 2-(5-ethoxycarbonylamino-1,2,4-thiadiazol-3-yl)acetate (52.8 mg; 2.15×10$^{-1}$ mmol), dimethyl sulfoxide (76.5 μl; 1.07 mmol), iodine (5.5 mg; 2.2× 10$^{-2}$ mmol) and concentrated sulfuric acid (0.6 μl) in ethyl acetate (528 μl) was treated in the same manner as in Example 5 to give methyl 2-oxo-2-(5-ethoxylcarbonylamino-1,2,4-thiadiazol-3-yl)acetate (40.8 mg; yield 73.2%) as white crystals.

m.p.: 170°–174° C. (hexane/ethyl acetate)

NMR δ(CDCl$_3$): 1.40(3H.t.CH$_3$CH$_2$O) 4.01(3H.s.CH$_3$O) 4.41(2H.q.CH$_2$O) 9.10(1H.bs.NH)

Anal. Calcd. for C$_8$H$_9$N$_3$O$_4$S: C,37.06;H,3.50;N,16.21 (%). Found: C,37.03;H,3.43;N,16.21(%).

EXAMPLE 7

A solution of methyl 2-(5-phenoxycarbonylamino-1,2,4-thadiazol-3-yl)acetate (53.0 mg; 1.81×10$^{-1}$ mmol), dimethyl sulfoxide (64.0 μl; 9.02×10$^{-1}$ mmol), iodine (4.6 mg; 1.8× 10$^{-2}$ mmol) and concentrated sulfuric acid (0.5 μl) in ethyl acetate (530 μl) was treated in the same manner as in Example 5 to give methyl 2-oxo-2-(5-phenoxycarbonylamino-1,2,4-thiadiazol-3-yl)acetate (24.4 mg; yield 43.9%).

m.p. 74°–79° C.

NMR δ(CDCl$_3$): 4.00(3H.s.CH$_3$) 7.25–7.49(5H.m.Ph) 9.45(1H.bs.NH)

EXAMPLE 8

A solution of methyl 2-(5-benzyloxycarbonylamino-1,2,4-thiadiazol-3-yl)acetate (64.0 mg; 2.08×10$^{-1}$ mmol), dimethyl sulfoxide (74.0 μl; 1.04 mmol), iodine (5.3 mg; 2.1× 10$^{-2}$ mmol) and concentrated sulfuric acid (0.6 μl) in ethyl acetate (640 μl) was treated in the same manner as Example 5 to give methyl 2-oxo-2-(5-benzyloxycarbonylamino-1,2,4-thiadiazol-3-yl)acetate (37.5 mg; yield 56.1%).

m.p. 144°–147° C. (hexane/ethyl acetate)

NMR δ(CDCl$_3$): 4.00(3H.s.CH$_3$), 5.35(2H.s.CH$_2$) 7.32–7.49(5H.m.Ph), 9.07(1H.bs.NH)

Anal. Calcd. for C$_{13}$H$_9$N$_3$O$_5$S:

C,48.60;H,3.45;N,13.08(%). Found: C,48.43;H,3.49;N, 13.06(%).

EXAMPLE 9

A solution of methyl 2-(5-methoxycarbonylamino-1,2,4-thiadiazol-3-yl)acetate (97.8 mg; 4.23×10$^{-1}$ mmol), dimethyl surfoxide (150 μl; 2.11 mmol), iodine (10.7 mg; 4.23×10$^{-2}$ mmol) and concentrated sulfuric acid (1.2 μl) in ethyl acetate (978 μl) was heated to reflux for 3 hours (at the bath temperature of 100° C.).

After the solution was allowed to cool, 95% aqueous methanol (978 μl) and methoxyamine hydrochloride (42,4 mg; 5.08×10$^{-1}$ mmol) were added to the reaction mixture under stirring at room temperature and then the reaction mixture was stirred at the same temperature for 30 minutes. After the reaction was completed, the reaction mixture was directly concentrated and the residue obtained was diluted with ethyl acetate (1.0 ml), washed with saturated aqueous sodium thiosulphate, saturated aqueous sodium bicarbonate, saturated aqueous sodium chloride, dried over sodium sulfate and then concentrated to give methyl 2-(5-methoxycarobonylamino-1,2,4-thiadiazol-3-yl)-2-methoxyiminoacetate (syn-isomer) (119 mg) as white crystals.

m.p. 158°–161° C.(hexane/ethyl acetate)

NMR δ(CDCl$_3$): 3.94(3H.s.NOCH$_3$), 3.97 (3H.s.COOCH$_3$) 4.12(3H.s.NHCOOCH$_3$), 8.58(1H.bs.NH)

Anal.Calcd.for C$_{13}$H$_{11}$N$_3$O$_5$S: C,48.60;H,3.45; N.13.08 (%). Found.: C,48.43;H,3.49;N,13.06(%).

EXAMPLE 10

A mixture of ethyl 2-(5-ethoxycarbonylamino-1,2,4-thiadiazol-3-yl) acetate (1.29 g; 5 mmol), dimethyl sulfoxide (7.1 ml; 100 mmol), iodine (127 mg; 0.5 mmol) and concentrated sulfuric acid (14 μl; 0.5 mmol) was heated with stirring for 4 hours (at bath temperature of 100° C.). After cooling, 95% aqueous methanol (13 ml) and methoxyamine hydrochloride (501 mg; 5×1.2 mmol) were added thereto and the reaction mixture was stirred for 3 hours at room temperature. Further, 5N sodium hydroxide aqueous solution (1.3 ml; 5×1.3 mmol) was added thereto and the mixture was stirred at room temperature for 1 hour. The solvent was thoroughly evaporated under reduced pressure and ethyl acetate (20 ml) was added to the residue. The mixture was washed with aqueous saturated sodium thiosulfate (2.5 ml), saturated aqueous sodium bicarbonate (2.5 ml) and saturated aqueous sodium chloride (2.5 ml×2), dried over sodium sulfate was concentrated to remove ethyl acetate and then dried under vacuum to give ethyl 2-(5-ethoxycarbonylamino-1,2,4-thiadiazol-3-yl)-2-methoxyiminoacetate (syn-isomer) (1.32 g; 87.6%).

m.p. 108°–110° C. (hexane/ethyl acetate)

IR(KBr)cm$^{-1}$: 2990, 1718, 1548, 1235, 1033.

$^1$HNMR δ(CDCl$_3$): 1.36(6H.t.J=7 Hz), 3.98(3H.s), 4.28 (2H.q.J=7 Hz), 4.36(2H.q.J=7 Hz), 7.56(1H.bs)

EXAMPLE 11

Ethyl 2-(5-benzyloxycarbonylamino-1,2,4-thiadiazol-3-yl)acetate (1.6 g; 5 mmol) was treated in the same manner as in Example 10 to give ethyl 2-(benzyloxycarbonylamino-1,2,4-thiadiazol-3-yl)-2-methoxyiminoacetate (syn-isomer) (1.6 g; 91.7%) as a syrup.

$^1$HNMR δ(CDCl$_3$): 1.34(3H.t.J=7 Hz), 3.92(3H.s) 4.36 (2H.q.J=7 Hz), 5.21(2H.s), 7.26(5H.s)

EXAMPLE 12

Ethyl 2-(5-benzyloxycarbonylamino-1,2,4-thiadiazol-3-yl)-2-methoxyiminoacetate (syn-isomer) (1.44 g; 4.11 mmol) was dissolved in ethanol (14 ml) and 2N NaOH (4.11 ml; 8.22 mmol) was added thereto at room temperature. The reaction mixture was stirred at the room temperature for 2 hours. Ethanol was evaporated under reduced pressure and the residue was dissolved in water (15 ml). The mixture was washed twice with ethyl acetate (10 ml) and acidified with 6N hydrochloric acid (1.6 ml) to pH 1. After cooling, the crystals formed were filtered off, washed with water and then dried under reduced pressure to give 2-(5-benzyloxycarbonylamino-1,2,4-thiadiazol-3-yl)-2-methoxyiminoacetic acid (syn-isomer) (1.02 g; 73.8%).

m.p. 138°–142° C.

IR (KBr$_6$)cm$^{-1}$: 3170, 1710, 1545, 1228, 1040.

$^1$HNMR δ(DMSO-d$_6$): 3.93(3H.s), 5.25(2H.s), 5.85 (2H.bs) 7.31(5H.s)

EXAMPLE 13

To ethyl 2-(5-ethoxycarbonylamino-1,2,4-thiadiazole-3-yl)-2-methoxyiminoacetate (syn-isomer) (302 mg; 1.0 mmol) was added 1N sodium hydroxide (6.0 ml; 6.0 mmol) and the reaction mixture was refluxed for 5 hours (at the bath temperature of 110° C.). After cooling, the mixture was acidified with 6N hydrochloric acid (1.0 ml) to pH 1. The mixture was extracted with ethyl acetate (0.3 ml×5) and the extract was dried over sodium sulfate and then concentrated to give 2-(5-amino-1,2,4-thiadiazol-3-yl)-2-methoxyiminoacetic acid (syn-isomer) (102 mg; 50,4%).

m.p. 179°–181° C.

EXAMPLE 14

A solution of ethyl 2-(5-ethoxycarbonylamino-1,2,4-thiadiazol-3-yl)-2-methoxyiminoacetate (19.6 mg; 7.15× 10$^{-2}$ mmol) in aqueous 1N NaOH solution (286 μl; 286× 10$^{-1}$ mmol) was stirred at 100° C. for 4 hours. After cooling, the mixture was acidified with 6N hydrochloric acid to pH 1. The mixture was extracted with ethyl acetate (0.3 ml×5) and the extract was dried over sodium sulfate and then concentrated to give 2-(5-amino-1,2,4-thiadiazol-3-yl)-2-methoxyiminoacetic acid (10.8 mg; yield 74.7%) as white crystals.

m.p. 179°–181° C.

NMR δ(DMSO-d$_6$): 3.90(3H.s.CH$_3$), 8.20(2H.bs. NH$_2$)

EXAMPLE 15

3-amino-5-methoxyisoxazole (1.2 g) was dissolved in tetrahydrofuran (10 ml) and benzoylisothiocyanate (2.2 g) was added dropwise thereto at 2°–3° C. After the mixture was stirred for 1 hour, the reaction mixture was poured into ice-water and then the formed crystals were filtered off. After washing with water and isopropylether, the crystals was dissolved in ethanol (50 ml) with warming. The solution was concentrated under reduced pressure to give methyl 2-(5-benzoylamino-1,2,4-thiadiazol-3-yl)acetate (1.6 g, 57.7%).

m.p. 143°–144.5° C.

NMR δ(CDCl$_3$): 3.68(3H.s,—COOOCH$_3$), 3.81(2H.s, CH$_2$), 7.05–8.0(5H,m,—C$_6$H$_5$)

IR(KBr)cm$^{-1}$ : 1720, 1660, 1540.

EXAMPLE 16

3-amino-5-ethoxyisoxazole (1.3 g), tetrahydrofuran (10 ml) and benzoylisothiocyanate (2.1 g) were treated in the same manner as in Example 15, to give ethyl 2-(5-benzoylamino-1,2,4-thiadiazol-3-yl) acetate 2.0 g (68.7%).

m.p. 119.0°–120.5° C.

NMR δ(CDCl$_3$): 1.2(3H,t,CH$_3$—) 3.7(2H,s.—CH$_2$—), 4.1(2H,q,—OCH$_2$), 7.2–8.1(5H,m,—C$_6$H$_5$), 11.2(1H,brs, NH)

IR(KBr)1270cm$^{-1}$: 1720, 1670, 1530.

EXAMPLE 17

A solution of 4-nitrobenzoyl chloride (3.8 g) and potassium thiocyanate (2.5 g) in toluene (20 ml) was heated with stirring at 80°–90° C. for 5 hours. After the insoluble matter was filtered, the filtrate was concentrated to give p-nitrobenzoylisothiocyanate 3.3 g. The product was dissolved in tetrahydrofuran (20 ml) and 3-amino-5-ethoxyisoxazole (2 g) was added thereto at 2°–4° C. After the reaction mixture was stirred for 2 hours, the mixture was poured into ice-water and the formed precipitates were filtered. After the precipitates were washed with water and isopropylether, ethanol (100 ml) was added thereto and the mixture was stirred at 40° C. for 30 minutes. After the formed precipitates were filtered, recrystallized with ethyl acetate/isopropyl ether to give ethyl 2-(5-(4-nitrobenzoylamino-1,2,4-thiadiazol-3-yl)acetate.

m.p. 178.0°–180.5° C.

NMR δ(DMSO-d$_6$): 3.9(2H,s,—CH$_2$—), 4.1(2H,q,—OCH$_2$—), 8.27(4H,s,C$_6$H$_4$—), 14(1H,brs,—NH), 1.17(3H, t,—CH$_3$)

IR(KBr)cm$^{-1}$: 1710, 1670, 1520–40.

EXAMPLE 18

3-amino-5-ethoxyisoxazole (1.3 g) was dissolved in tetrahydrofuran (10 ml) and 3,4-difluoroisocyanate (1.7 g) was added thereto. The mixture was reacted at 2°–3° C. for 1.5 hours and then at room temperature. After the solvent was evaporated, water was added thereto and the crystals were filtered. The obtained crystals were dissolved with ethanol and the mixture was warmed at 40°–50° C. for 30 minutes and then concentrated to give ethyl 2-(5-(3,4-difluorophenylamino)-1,2,4-thiadiazol-3-yl) acetate (0.25 g).

m.p. 84°–90° C.

NMR δ(CDCl$_3$): 1.27(3H,t,CH$_3$—), 3.77(2H,s,—CH$_2$—), 4.17(2H,q,—OCH$_2$CH$_3$), 6.83–7.57(3H,m,C$_6$H$_3$F$_2$—), 8.83(1H,brs,NH)

IR(KBr)cm$^{-1}$: 1700, 1620, 1560, 1510.

EXAMPLE 19

A solution of methyl 2-(5-benzoylamino-1,2,4-thiadiazol-3-yl) acetate (5 g), dimethyl sulfoxide (24 ml) and iodine (0.63 g) in concentrated sulfuric acid (0.064 ml) was heated at 100° C. for 4 hours and cooled. Then ethyl acetate (200 ml) was added thereto. The mixture was washed with saturated aqueous sodium thiosulfate, saturated aqueous sodium bicarbonate and saturated aqueous sodium chloride, dried over sodium sulfate and concentrated to give methyl 2-(5-benzoylamino-1,2,4-thiadiazol-3-yl)-2-oxo-acetate 1.4 g.

m.p. 164°–166.5° C.

NMR δ(CDCl$_3$): 3.95(3H,s,COOCH$_3$), 7.1–8.1(5H,m, C$_6$H$_5$—), 14.1(1H,brs,—CONH)

IR(KBr)cm$^{-1}$: 1720–1700, 1520, 1280.

EXAMPLE 20

Ethyl 2-(5-benzoylamino-1,2,4-thiadiazol-3-yl)acetate (2 g), dimethyl sulfoxide (12 ml), iodine (0.19 g) and concentrated sulfuric acid (0.019 ml) were treated in the same manner as in Example 19 to give ethyl 2-(5-benzoylamino-1,2,4-thiadiazol-3-yl)-2-oxo-acetate 0.7 g.

m.p. 178°–179.5° C.

NMR δ(CDCl$_3$): 1.0(3H,t,—CH$_3$), 4.4(2H,q, COOCH$_2$CH$_3$), 7.3–8.2(5H,m,C$_6$H$_5$), 14.2(1H,brs,—CONH)

IRcm$^{-1}$: 1720–1700, 1660, 1530, 1280.

EXAMPLE 21

A solution of methyl 2-(5-methoxycarbonylamino-1,2,4-thiadiazol-3-yl)-2-methoxyiminoacetate (13.7 g, 0.05 mol) and sodium hydroxide (4.49 g, 0.11 mol) in water (112 ml) was reacted with stirring for 1 hour. After the reaction was completed, the reaction mixture was acidified to pH 1 with 35% hydrochloric acid, extracted with ethyl acetate and dried over sodium sulfate and concentrated to give 2-(5-methoxycarbonylamino-1,2,4-thiadiazol-3-yl)-2-methoxyiminoacetic acid 9.8 g (yield 75.7%).

m.p. 178°–180° C. (decomposition)

EXAMPLE 22

A solution of methyl 2-(5-benzoylamino-1,2,4-thiadiazol-3-yl)-2-methoxyiminoacetate (32 g, 0.1 mol), sodium hydroxide (16 g, 0.4 mol) in water (400 ml) was reacted with stirring at room temperature for 3 hours. After the reaction was completed, the reaction mixture was acidified to pH 1 with 35% hydrochloric acid and the formed precipitates were filtered off and washed with water and isopropyl ether and then dried under reduced pressure to give 2-(5-benzoylamino-1,2,4-thiadiazol-3-yl)-2-methoxyiminoacetic acid 29.7 g (yield 97.4%).

m.p. 198°–200° C. (decomposition)

EXAMPLE 23

(a) 2-(5-methoxycarbonylamino-1,2,4-thiadiazol-3-yl)-2-methoxyiminoacetic acid (5 g, 0.019 mol), 25% aqueous ammonia (7.1 g) and water (93 g) were charged in a pressure container and heated at 100° C. for 40 hours. After completion of the reaction, the reaction mixture was distilled under reduced pressure to remove ammonia and then acidified with 2N hydrochloric acid to pH 1 and extracted with ethyl acetate. The extract was dried over sodium sulfate and concentrated to give white crystals (3.5 g). White crystals obtained as above were recrystallized from methanol/H$_2$O and the obtained crystals were dried under reduced pressure to give 2-(5-amino-1,2,4-thiadiazol-3-yl)-2-methoxyiminoacetic acid (1.75 g, yield 45%).

Purity: by HPLC 85%

(b) 2-(5-benzoylamino-1,2,4-thiadiazol-3-yl)-2-methoxyiminoacetic acid (20 g, 0.065 mol) and 14% aqueous ammonia were charged in 500 ml pressure container and heated at 100° C. 40 hours. After completion of the reaction, the reaction mixture was distilled to remove ammonia and concentrated to about half volume. The concentrate was acidified with 2N HCl to pH 2–3 and extracted with ethyl acetate. The aqueous layer was acidified with concentrated HCl to pH 1, and sodium chloride was added thereto. Then the solution was extracted with ethyl acetate and the extract was dried over sodium sulfate and concentrated to give white crystals (10 g).

White crystals as above described was washed with ethyl acetate and dried under reduced pressure to give 2-(5-amino-1,2,4-thiadiazol-3-yl)-2-methoxyiminoacetic acid (yield 9.6 g, 78.6%).

Purity: by HPLC 97.5% m.p. 174°–175° C. (decomposition)

(c) A solution of 2-(5-benzoylamino-1,2,4-thiadiazol-3-yl)-2-methoxyiminoacetic acid (7.5 g, 0.0245 mol) and diethanolamine (12.9 g, 0.123 mol) in water (130 g) was heated at 100° C. for 24 hours. After completion of the reaction, the reaction mixture was applied to column of strong acid cation exchange resin (150 ml) and the resin was washed with ion exchange water (1000 ml). The eluent was combined with washings and the mixture was concentrated to about 300 ml. The concentrate was extracted with isopropyl ether and aqueous layer was concentrated. The formed crystals were filtered off and dried under reduced pressure to give 2-(5-amino-1,2,4-thiadiazol-3-yl)-2-methoxyiminoacetic acid (4.2 g, yield 84.8%).

Purity: by HPLC 96.2%

(d) A solution of 2-(5-benzoylamino-1,2,4-thiadiazol-3-yl)-2-methoxyiminoacetic acid (153 mg) in 5% aqueous butylamine was reacted at 100° C. for 40 hours to give 2-(5-amino-1,2,4-thiadiazol-3-yl)-2-methoxyiminoacetic acid.

(e) A solution of 2-(5-benzoylamino-1,2,4-thiadiazol-3-yl)-2-methoxyiminoacetic acid (200 mg) in 8% aqueous methylamine (2.5 ml) was reacted at 100° C. for 40 hours to give 2-(5-amino-1,2,4-thiadiazol-3-yl)-2-methoxyiminoacetic acid.

EXAMPLE 24

(a) To a suspension of potassium thiocyanate (47.5 g, 0.49 mol) in acetonitrile 300 ml was added dropwise methyl chloroformate (43.0 g, 0.46 mol) and the mixture was stirred at 70° C. for 30 minutes. Then 3-aminoisoxazole (29.4 g, 0.35 mol) was added dropwise to the mixture under ice-cooling and stirring. The mixture was stirred for 30 minutes at the same temperature and then for 15 minutes at room temperature. The reaction mixture was poured into ice-water (800 ml) and the precipitates formed were filtered off, washed with water and then dried under reduced pressure to give 1-(isoxazol-3-yl)-3-methoxycarbonylthiourea (36 g).

Yield 51.2%. m.p. 165°–167° C. (ethyl acetate/hexane).

NMR δ(CDCl$_3$): 3.85(3H,s,COOCH$_3$), 7.36(1H,w,J=2 Hz), 8.28(1H,w,J=2 Hz), 8.50(1H,bs,—NHCS—), 10.50 (1H,bs,NH).

IR(KBr)cm$^{-1}$: 1730, 1596, 1549, 1342, 1245, 1200.

(b) 1-(isoxazol-3-yl)-3-methoxycarbonylthiourea (30 g, 0.15 mol) obtained in Example 24(a) as described above was heated in methanol (200 ml) at 30°–35° C. for 1 hour. After cooling, the crystals formed were filtered off. Isopropyl ether (50 ml) was added to the mother liquor and the precipitates formed were filtered off, combined with the former crystals and concentrated under reduced pressure to give 2-(5-methoxycarbonylamino-1,2,4-thiadiazol-3-yl)acetaldehyde (28.5 g). Yield 98%.

m.p. 164°–166° C. (MeOH).

NMR δ(CDCl$_3$): 3.90(2H,w,J=2 Hz), 3.92(3H,s, COOCH$_3$), 9.87(1H,t,CHO), 10.50(1H,bs,NH).

IR(KBr)cm$^{-1}$: 2955, 1720, 1565, 1295, 1245, 1110.

(c) 2-(5-methoxycarbonylamino-1,2,4-thiadiazol-3-yl) acetaldehyde (3.72 g, 18.5 mmol) obtained in Example 24(b) as described above was dissolved in a mixture of t-butanol (50 ml) and water (5 ml) and then peracetic acid (20 ml, 86.8 mmol) was added dropwise thereto under ice-cooling. The temperature was elevated to 20° C. and then the reaction mixture was stirred overnight at the same temperature while the reaction was continued. After completion of the reaction, excess peracetic acid was decomposed with aqueous 30% sodium bisulfite solution and then the crystals formed were filtered off. The filtrate was concentrated up to ⅓ the original volume of and the crystals formed was filtered off after cooling. The crystals were combined with the former crystals and then dried under reduced pressure to give 2-(5-methoxycarbonylamino-1,2,4-thiadiazol-3-yl)acetic acid (3.2 g). Yield 80.0%.

m.p. 188°–190° C. (MeOH)

NMR δ(DMSO-d$_6$): 3.90(2H,w,J=2 Hz), 3.92(3H,s), 10.50(1H,bs,—NH—).

IR(KBr)cm$^{-1}$: 2959, 1720, 1555, 1355.

EXAMPLE 25

(a) A suspension of ethyl chloroformate (6.51 g, 0.06 mol) and potassium thiocyanate (6.31 g, 0.065 mol) in acetonitrile (60 ml) was treated with 3-aminoisoxazole (4.2 g, 0.05 mol) in the same manner as Example 24(a) and the precipitates formed were filtered off, washed with water and then dried under reduced pressure (yield 5.20 g).

This product was identified to be a mixture of 1-(isoxazol-3-yl)-3-ethoxycarbonylthiourea and 2-(5-ethoxycarbonylamino-1,2,4-thiadiazol-3-yl)-acetaldehyde by NMR analysis.

NMR δ(CDCl$_3$): 1.24(t,J=7 Hz), 3.92(w,J=2 Hz), 4.23(q, J=7 Hz), 7.38(w,J=2 Hz), 8.28(w,J=2 Hz), 9.05(bs,—NHCS—), 9.87(t,CHO), 10.50(bs,NH).

(b) The crystals obtained (5.16 g) in Example 25(a) as described above were heated in methanol (100 ml) at 40°–45° C. for 2 hours and treated then in the same manner. The crystals were filtered off and dried under reduced pressure to give 2-(5-ethoxycarbonylamino-1,2,4-thiadiazol-3-yl)acetaldehyde (4.90 g). Yield 45.6% (from 3-aminoisoxazole).

m.p. 152°–154° C.(MeOH)

NMR δ(CDCl$_3$): 1.23(3H,t,J=7 Hz), 3.90(2H,w,J=2 Hz), 4.22 (2H,q,J=7 Hz) 9.87(1H,t,CHO), 10.50(1H,bs,NH)

IR(KBr)cm$^{-1}$: 2960, 1719, 1580, 1275, 1245.

(c) 2-(5-ethoxycarbonylamino-1,2,4-thiadiazol-3-yl) acetaldehyde (4.02 g, 18.7 mmol) obtained in Example 25(b) as described above was dissolved in ethyl acetate (70 ml) and treated in the same manner as in Example 24(c) the crystals were filtered off and dried under reduced pressure to give 2-(5-ethoxycarbonylamino-1,2,4-thiadiazol-3-yl)acetic acid (3.4 g). (yield 78%).

m.p. 170°–172° C.(MeOH)

NMR (DMSO-d$_6$): 1.24 (3H,t,J=7 Hz), 3.91(2H,W,J=2 Hz), 4.24(2H,g,J=7 Hz), 10.52(1H,bs,NH).

IR(KBr)cm$^{-1}$: 2962, 1719, 1557, 1358.

EXAMPLE 26

(a) A suspension of acetyl chloride (9.42 g, 0.12 mol) and potassium thiocyanate (12.62 g, 0.13 mol) in acetonitrile (100 ml) was heated at 70° C. for 3 hours and then 3-aminoisoxazole (8.4 g, 0.1 mol) was added dropwise thereto under ice-cooling and stirring. The mixture was stirred for 1 hour at the same temperature and then for 1 hour at room temperature. Then the reaction mixture was poured into ice-water (250 ml) and the mixture was stirred for 1 hour. The precipitates formed were filtered off, washed with water and then dried under reduced pressure (yield 7.5 g).

This product was identified to be a mixture of 1-(isoxazol-3-yl)acetylthiourea and 2-(5-acetylamino-1,2,4-thiadiazol-3-yl)acetaldehyde by NMR analysis.

NMR δ(CDCl$_3$): 2.25(s,COCH$_3$), 3.90(w,J=2 Hz), 7.33 (w,J=2 Hz), 8.88(w,J=2 Hz), 9.87(t,CHO), 10.81(bs,—NHCS—), 12.60(bs,—NH—)

(b) The crystals (7.45 g) obtained in Example 26(a) as described above were heated in methanol (150 ml) at 40°–45° C. for 1 hour and treated in the same manner as in Example 25. The crystals were filtered off and dried under reduced pressure to give 2-(5-acetylamino-1,2,4-thiadiazol-3-yl)acetaldehyde (7.05 g). Yield 32% (from 3-aminoisoxazole).

m.p. 145°–147° C. (MeOH)

NMR δ(CDCl$_3$): 2.23(3H,s), 3.92(2H,w,J=2 Hz), 9.87 (1H,t,CHO), 10.80(1H,b,—NH—).

IR(KBr)cm$^{-1}$: 2955, 1695, 1660, 1575, 1225.

(c) 2-(5-acetylamino-1,2,4-thiadiazol-3-yl)acetaldehyde (6.2 g, 33.5 mmol) obtained in Example 26(b) as described above was dissolved in ethyl acetate (100 ml), and treated in the same manner as Example 25(c). The crystals were filtered off and dried under reduced pressure to give 2-(5-acetylamino-1,2,4-thiadiazol-3-yl)acetic acid (5.1 g, yield 75%).

m.p. 161°–163° C.(MeOH)

NMR δ(DMSO-d$_6$): 2.24(3H,s), 3.93(2H,W,J=2 Hz), 16.80(1H,bs,—NH—)

IR(KBr)cm$^{-1}$: 2958, 1698, 1665, 1550.

EXAMPLE 27

(a),(b) A suspension of phenylchloroformate (2.9 g, 18.5 mmol) and potassium thiocyanate (1.95 g, 20 mmol) in acetonitrile (20 ml) was treated with 3-aminoisoxazole (1.4 g, 16.7 mmol) and treated in the same manner as in Example 24(a),(b). The crystals were filtered off and dried under reduced pressure to give 2-(5-phenoxycarbonylamino-1,2,4-thiadiazol-3-yl)acetaldehyde (1.1 g, yield 25%).

m.p 159°–162° C.(MeOH)

NMR δ(CDCl₃): 3.92(2H,W J=2 Hz), 7.15–7.53(5H,m, ph), 9.87(1H,t,CHO), 10.85(1H,bs,—NH—)

IR(KBr)cm⁻¹: 3090, 1729, 1590.

(c) 2-(5-phenoxycarbonylamino-1,2,4-thiadiazol-3-yl) acetaldehyde (1.0 g, 3.8 mmol) was dissolved in dichloroethane (30 ml) and treated in the same manner as in Example 24(c). The crystals were filtered off and dried under reduced pressure to give 2-(5-phenoxycarbonylamino-1,2,4-thiadiazol-3-yl)acetic acid (798 mg, yield 75%).

m.p. 174°–176° C. (MeOH)

NMR δ(DMSO-d₆): 3.92(2H,W,J=2 Hz), 7.16–7.54(5H, m,ph), 10.86(1H,bs,—NH—).

IR(KBr)cm⁻¹: 3095, 1730, 1595.

EXAMPLE 28

(a) A suspension of benzoyl chloride (9 g, 64.3 mmol) and potassium thiocyanate (11.3 g, 0.116 mmol) in acetonitrile (40 ml) was heated at 70° C. for 6 hours and then cooled. Potassium chloride was filtered, acetonitrile was removed from the filtrate and the residue was dried under reduced pressure to give benzoylisothiocyanate (6.3 g, 95°–96° C./5 mmHg).

The obtained benzoylisothiocyanate (6.3 g, 38.7 mmol) was dissolved in acetonitrile (50 ml). 3-aminoisoxazole (2.8 g, 33.3 mmol) was added dropwise thereto. The mixture was stirred at the same temperature for 1 hour and then treated in the same manner as in Example 26(a). The crystals were filtered off and dried under reduced pressure to give a mixture (6.5 g) of 1-(isoxazol-3-yl)-benzoylthiourea and 2-(5-benzoylamino-1,2,4-thiadiazol-3-yl)acetaldehyde.

(b) The crystals (6.5 g) obtained in Example 28(a) as described above were treated in the same manner as in Example 26(b) and the crystals were filtered off and dried under reduced pressure to give 2-(5-benzoylamino-1,2,4-thiadiazole-3-yl)acetaldehyde (6.4 g). Yield 77.5% (from 3-aminoisoxazol).

m.p. 153°–155° C.(MeOH)

NMR δ(CDCl₃): 3.92(2H,W,J=2 Hz), 7.63–8.26(5H,m, ph), 9.86(1H,t,CHO), 10.84(1H,bs,—NH—).

IR(KBr)cm⁻¹: 3010, 1698, 1662, 1570.

(c) 2-(5-benzoylamino-1,2,4-thiadiazol-3-yl) acetaldehyde (6 g, 24.2 mmol) obtained in Example 28(b) as described above was dissolved in dichloroethane (180 ml) and treated then in the same manner as in Example 24(c). The crystals were filtered off and dried to give 2-(5-benzoylamino-1,2,4-thiadiazol-3-yl)acetic acid (4.98 g, yield 78%).

m.p. 173°–175° C. (MeOH)

NMR δ(DMSO-d₆): 3.92(2H,W,2 Hz), 7.63–8.26(5H,m, ph), 10.85 (1H,bs,—NH—).

IR(KBr)cm⁻¹: 3014, 1670, 1560.

EXAMPLE 29

(a),(b) A suspension of p-nitrophenyl chloroformate (4.07 g, 20.2 mmol) and potassium thiocyanate (2.12 g, 21.7 mmol) in acetonitrile (100 ml) was treated with 3-aminoisoxazole (1.3 g, 15.5 mmol) in the same manner as in Example 24-(a),(b). The crystals were filtered off and dried under reduced pressure to give 2-(5-p-nitrophenoxycarbonylamino-1,2,4-thiadiazol-3-yl) acetaldehyde (0.91 g). Yield 20%.

m.p. 172°–175° C.(MeOH)

NMR δ(CDCl₃): 3.92 (2H,W,J=2 Hz), 7.68–8.83(4H,m, ph), 9.87 (1H,t,CHO), 10.86 (1H,bs,—NH—).

IR(KBr)cm⁻¹: 3092, 1730, 1595.

(c) 2-(5-p-nitrophenoxycarbonylamino-1,2,4-thiadiazol-3-yl)acetaldehyde (0.8 g, 2.7 mmol) was dissolved in dichloroethane (20 ml) and treated in the same manner as in Example 24(c). The crystals were filtered off and dried under reduced pressure to give 2-(5-p-nitrophenoxycarbonylamino-1,2,4-thiadiazol-3-yl)acetic acid (0.71 g). Yield 84%.

EXAMPLE 30

3-aminoisoxazole (155 g) was dissolved in tetrahydrofuran (776 ml) and benzoylisothiocyanate (354 g) was added dropwise thereto. The reaction mixture was poured into ice-water after stirring for 1 hour and 1-(isoxazol-3-yl) benzoylthiourea was filtered off. This crystals were dissolved in ethanol (2200 ml) and the solution was heated at 50° C. for 30 minutes and then cooled to give 2-(5-benzoylamino-1,2,4-thiadiazol-3-yl)-1-ethoxy-1-ethanol (454 g, 83.8%).

m.p. 127°–128° C.(decomposition)

NMR δ(DMSO-d₆): 1.05(3H,t,—CH₂—CH₃), 2.70(2H, W,—CH₂—), 3.50(2H,m,O—CH₂—CH₃), 5.10(1H,q,—CH=), 6.08(1H,W,—OH), 7.52–8.25(5H,m,ph), 13.4 (1H, bs,—NH—)

IR(KBr)cm⁻¹: 3161, 1664, 1548, 1323, 1128.

EXAMPLE 31

1-(isoxazol-3-yl)benzoylthiourea obtained from 3-aminoisoxazole (7.8 g) in the same manner as Example 30 was dissolved in acetone and the solution was allowed to react overnight at ordinary temperature and then cooled to give 2-(5-benzoylamino-1,2,4-thiadiazol-3-yl)acetaldehyde (4.7 g, yield 38%).

m.p. 149° C.–152° C. (decomposition)

NMR δ(DMSO-d₆): 4.0(2H,d,—CH₂—),7.4–8.2(5H,m, ph), 9.7(1H,t,CHO), 13.3(1H,brs,—NH—), IR(KBr)cm⁻¹: 1668, 1540, 1290.

EXAMPLE 32

2-(5-benzoylamino-1,2,4-thiadiazol-3-yl)-1-ethoxy-1-ethanol (60 g) was dissolved in acetic acid (600 g) and 38% peracetic acid (48 g) was added dropwise thereto at 40° C. After the mixture was reacted for 6.5 hours, aqueous sodium bisulfite was added thereto and acetic acid was removed by distillation of the mixture. The concentrate was poured into water and the precipitated 2-(5-benzoyl-1,2,4-thiadiazol-3-yl)acetic acid was filtered off. yield 51.3 g (95.3%)

m.p.172°–174° C.

NMR δ(DMSO-d₆): 3.87(2H,s,—CH₂—), 7.52–8.25(5H, m,ph)

IR(KBr)cm⁻¹: 3172, 1693, 1668, 1545, 1286.

EXAMPLE 33

4-fluorobenzoylchloride (79.2 g) and potassium thiocyanate (58.6 g) was refluxed in toluene (200 ml) for 10 hours. The reaction mixture was distilled to give 4-fluorobezoylisothiocyanate (69.7 g). The product obtained as above (24 g) was dissolved in tetrahydrofuran (100 ml), 3-aminoisoxazole 10 g was added dropwise at 0°–3° C. and the mixture was stirred. The reaction mixture was poured into ice-water and the precipitate formed was filtered off and washed with water and isopropylether. The obtained thiourea derivative was dissolved in ethanol and the solution was stirred at 40°–50° C. 5-(4-fluorobenzoylamino-1,2,4-thiadiazol-3-yl)acetaldehyde hemiacetal was formed and filtered off. Yield 22.5 g(60.2%).

m.p. 129°–131° C.

NMR δ(DMSO-d$_6$) 1.1(3H,t,—CH$_3$), 3.0(2H,W,—CH$_2$), 3.2–3.9 (m,2H,—O—CH$_2$), 5.1 (1H,q,CH), 6.1(1H,W,OH), 7.1–8.3(m,4H,ph), 13.5 (1H,bs,NH)

IR(KBr)cm$^{-1}$: 1666, 1597, 1551, 1514, 1311.

EXAMPLE 34

5-(4-fluorobenzoylamino)-1,2,4-thiadiazol-3-yl) acetaldehyde hemiacetal (20 g) was dissolved in acetic acid (200 ml) and 39% peracetic acid (17.7 g) was added thereto. After the mixture was allowed to react overnight at 40°–45° C., an aqueous sodium hydrogensulfite aqueous solution was added thereto. The reaction mixture was concentrated under reduced pressure and then the concentrate was treated in the same manner as in Example 32 to give 5-(4-fluorobenzoylamino)-1,2,4-thiadiazol-3-yl)acetic acid (9.4 g, yield 76%).

m.p. 189.5°–191.0° C.

NMR δ(DMSO-d$_6$): 3.9(2H,s,—CH$_2$—), 7.2–8.4(4H,m, ph)

IR(KBr)cm$^{-1}$: 1693.4, 1672.2, 1598.9, 1544.9, 1242.1.

EXAMPLE 35

1-(isoxazol-3-yl)-benzoylthiourea obtained from 3-aminoisoxazole (3.2 g) in the same manner as in Example 30, was dissolved in methanol and the mixture was heated at 40° C. for 1.5 hours. The mixture was cooled to give 2-(5-benzoylamino-1,2,4-thiadiazol-3-yl)-1-methoxy-1-ethanol (8.6 g, 80%).

m.p. 103°–105° C.(decomposition)

NMR δ(DMSO-d$_6$): 2.52 (2H,W,—CH$_2$), 3.05(3H,S.—OCH$_3$), 4.83(1H,q,—CH=), 5.98(1H,W,—OH), 7.25–7.95 (5H,m,ph), 13.3 (1H,bs,NH)

IR(KBr)cm$^{-1}$: 3350, 1647, 1579, 1552, 1332, 1114.

EXAMPLE 36

(A) Into a solution of methyl 2-(5-methoxycarbonylamino-1,2,4-thiadiazol-3-yl)acetate (230 mg, 9.96×10$^{-1}$ mmol) and concentrated hydrochloric acid (12.4 ml, 1.49×10$^{-1}$ mmol) in tetrahydrofuran (2.30 ml) was bubbled, over 10 minutes, methyl nitrite (MeONO) gas which was prepared by gradually dropping 12N hydrochloric acid aqueous solution (500 μl, 6.00 mmol) to a suspension of sodium nitrite (137 mg, 1.99 mmol) in 50% aqueous methanol (242 μl). The reaction mixture was directly concentrated after stirring for 1 hour at the same temperature. Ether (5 ml) was added to the obtained residue. White crystals formed were filtered off, washed with ether (1 ml×3) and then dried under reduced pressure to give methyl (Z)-2-hydroxyimino-2-(5-methoxycarbonylamino-1,2,4-thiadiazol-3-yl)acetate (227 mg, yield 87.6%).

m.p. 187°–190° C. (CHCl$_3$)

NMR (CDCl$_3$): 3.96 (3H,s,COOCH$_3$), 4.02 (3H,s, NHCOOCH$_3$), 9.45(1H,bs,NH or NOH), 9.92(1H,bs,NOH or NH)

Anal. Calcd. for C$_7$H$_8$N$_4$O$_5$S:

C,32.31;H,3.10;N,21.53 (%). Found: C,32.17;H,2.99;N, 21.42(%).

(B) To a suspension of methyl (Z)-2-hydroxyimino-2-(5-methoxycarbonylamino-1,2,4-thiadiazol-3-yl)acetate (21.1 mg, 8.11×10$^{-2}$ mmol), barium oxide (62.2 mg, 4.05×10$^{-1}$ mmol) and barium hydroxide 8 hydrate (12.8 mg, 4.05×10$^{-2}$ mmol) in dimethylformamide (422 μl) and chloroform (150 μl), was added dimethyl sulfate (8.4 μl, 8.9×10$^{-2}$ mmol) under stirring at room temperature. The reaction mixture was diluted with ethyl acetate (0.5 ml) after stirring for 30 min at the same temperature. Pieces of dry ice were added thereto. The resulting insoluble matter was filtered through a layer of Celite and the residue was washed with ethyl acetate (0.5 ml×3). The filtrate was combined with the washings and the mixture was washed with saturated sodium chloride, dried over sodium sulfate and then concentrated to give methyl (Z)-2-(5-methoxycarbonylamino-1,2,4-thiadiazol-3-yl)-2-methoxy-iminoacetate (13.2 mg, yield 59.3%) as white crystals.

m.p. 158°–161° C. (However, either barium oxide or barium hydroxide only was used in the reaction (E)-isomer was formed.)

(C) A solution of methyl (Z)-2-(5-methoxycarbonylamino-1,2,4-thiadiazol-3-yl)-2-methoxyiminoacetate (19.6 mg, 7.15×10$^{-2}$ mmol) in aqueous 1N sodium hydroxide (286 μl, 2.86×10$^{-1}$ mmol) was stirred for 4 hours at 100° C., and then 1N hydrochloric acid (290 μl, 2.90×10$^{-1}$ mmol) was added dropwise thereto under ice-cooling and stirring (pH=1). The mixture was extracted with ethyl acetate (0.3 ml×5), and the extract was dried over sodium sulfate and then concentrated to give (Z)-2-(5-amino-1,2,4-thiadiazol-3-yl)-2-methoxyiminoacetic acid (10.8 mg, yield 74.7%) as white crystals.

NMR δ(DMSO-d$_6$): 3.90(3H,s,CH$_3$), 8.20(2H,bs,NH$_2$)

EXAMPLE 37

(A) A solution of methyl chloroformate (53.3 μl, 6.90×10$^{-1}$ mmol) and potassium thiocyanate (72.6 mg, 7.47×10$^{-1}$ mmol) in anhydrous tetrahydrofuran (575 μl) was stirred for 1 hour at 70° C., and then 3-amino-5-methoxyisoxazole (65.6 mg, 57.5×10$^{-1}$ mmol) was added to the reaction mixture under ice-cooling and stirring. The mixture was stirred for 30 minutes at the same temperature and further for 12 hours at room temperature. After the reaction was completed, residual potassium thiocyanate was decomposed by adding water (72.6 μl) to the reaction mixture at the same temperature and then residual potassium thiocyanate was disintegrate by stirring for 3 hours to give methyl (5-amino-1,2,4-thiadiazol-3-yl)acetate. Then concentrated hydrochloric acid (10.0 μl) was added to the product and methyl nitrite (1.73 mmol; prepared from 120 mg sodium nitrite, 140 μl 50% aqueous methanol, 500 μl 12N H$_2$SO$_4$) was bubbled thereinto. The reaction mixture was directly concentrated after stirring at the room temperature for 1 hour, the residue was dissolved in ethyl acetate (500 μl). The solution was washed with saturated aqueous sodium chloride, dried over sodium sulfate and then concentrated to give methyl (Z)-2-(5-methoxy-carbonylamino-1,2,4-thiadiazol-3-yl)2-hydroxyiminoacetate (124 mg, yield 82.9%) as pale yellow crude crystals.

(B) A suspension of methyl (Z)-2-hydroxyimino-2-(5-methoxycarbonylamino-1,2,4-thiadiazol-3-yl)acetate (21.6 mg, 8.30×10$^{-2}$ mmol), ethyl bromoacetate (10.1 μl, 9.13×10$^{-2}$ mmol), barium oxide (63.6 mg, 4.15×10$^{-2}$ mmol) and barium hydroxide 8 hydrate (21.0 mg, 6.64×10$^{-2}$ mmol) in dimethylformamide (400 μl) and chloroform (200 μl) was stirred for 1.5 hours under ice-cooling. After the reaction was completed, the reaction mixture was diluted with ethyl acetate. Pieces of dry ice were added thereto. The resulting insoluble matter was filtered through a layer of Celite. The residue was washed with ethyl acetate (0.5 ml×3), the filtrate was combined with the washings and the mixture was washed with saturated aqueous sodium chloride, dried over sodium sulfate and then concentrated to give methyl (Z)-2-ethoxy-carobonylmethloxyimino-2-(5-methoxycarbonylamino-1,2,4-thiadiazol-3-yl)acetate as yellow crude crystals (24.2 mg, yield 84.2%).

EXAMPLE 38

Ethyl (Z)-2-(5-benzyloxycarbonylamino-1,2,4-thiadiazol-3-yl)-2-methoxyiminoacetate 1.44 g (4.11 mmol) was dissolved in ethanol (14 ml) and 2N sodium hydroxide solution (4.11 ml, 8.22 mmol) was added thereto at room temperature. The mixture was stirred at room temperature for 2 hours. Ethanol was evaporated under reduced pressure. The residue was dissolved in water (15 ml), washed with ethyl acetate (10 ml) twice, acidified with 6N hydrochloric acid (1.6 ml) to pH 1. The reaction mixture was cooled and the crystals formed were filtered off, washed with water and then dried under reduced pressure to give (Z)-2-(5-benzyloxycarbonylamino1,2,4-thiadiazol-3-yl)-2-methoxyiminoacetic acid (1.02 g, 73.8%).

m.p. 138°–142° C.

IR(KBr)cm$^{-1}$: 3170, 1710, 1545, 1228, 1040.

$^1$HNMR δ(DMSO-d$_6$): 3.93(3H,s), 5.25(2H,s), 5.85(2H, bs), 7.31(5H,s)

EXAMPLE 39

To ethyl (Z)-2-(5-ethoxycarbonylamino-1,2,4-thiadiazol-3-yl)-2-methoxyiminoacetate (302 mg, 1.0 mmol) was added 1N sodium hydroxide (6.0 ml, 6.0 mmol) and the mixture was refluxed for 5 hours at the bath temperature of 110° C. The reaction mixture was cooled, acidified with 6N hydrochloric acid (1.0 ml) to pH 1 and extracted with ethyl acetate (4 ml). The extract was dried over sodium sulfate and then concentrated to give (Z)-2-(5-amino-1,2,4-thiadiazol-3-yl)-2-methoxyiminoacetic acid (102 mg, 50.4%)

The physicochemical data of the product corresponded to those of the product obtained in Example 36(c).

EXAMPLE 40

To a suspension of methyl (Z)-2-hydroxyimino-2-(5-methoxycarbonylamino-1,2,4-thiadiazol-3-yl)acetate (10.5 mg, 4.03×10$^{-2}$ mmol) and silver oxide (28.1 mg, 1.21×10$^{-1}$ mmol) in anhydrous dimethylformamide (100 ml) was added, methyl iodide (7.5 µl, 1.21×10$^{-1}$ mmol) under stirring at room temperature. The reaction mixture was stirred for 1 hour and then filtered through a layer of Celite. The residue was washed with ethyl acetate (1.0 ml×3). The filtrate was combined with washings and the mixture was concentrated to give crude syrup (17.3 mg, 100%). This was purified by column chromatography (0.3 g Kiesergel, hexane/ethyl acetate: 1/1) to give methyl (Z)-2-(5-methoxy-carbonylamino-1,2,4-thiadiazol-3-yl)-2-methoxyiminoacetate as white crystals (8.8 mg, 79.6%).

EXAMPLE 41

To a suspension of methyl (Z)-2-hydroxyimino-2-(5-methoxy-carbonylamino-1,2,4-thiadiazol-3-yl)acetate (7.2 mg, 2.8×10$^{-2}$ mmol), barium oxide(2.33 mg, 1.52×10$^{-1}$ mmol) and barium hydroxide 8 hydrate (7.0 mg, 2.2×10$^{-2}$ mmol) in anhydrous dimethylformamide (150 µl) and anhydrous chloroform (60 µl) was added, methyl iodide (2.1 µl, 3.3×10$^{-2}$ mmol) was added under stirring at room temperature. The reaction mixture was stirred at the same temperature for 30 minutes and then diluted with ethyl acetate (0.5 ml). Pieces of dry ice broken was introduced thereto. The insoluble matter was filtered through a layer of Celite and the residue washed with ethyl acetate (0.5 ml×3). The filtrate was combined with the washings and the mixture was washed with saturated sodium chloride, dried over sodium sulfate and concentrated to give methyl (Z)-2-(5-methoxycarbonylamino-1,2,4-thiadiazol-3-yl)-2-methoxyiminoacetate as white crystals (4.9 mg, yield 64%).

m.p. 158°–161° C.(hexane/ethyl acetate)

EXAMPLE 42

To a suspension of methyl (Z)-2-hydroxyimino-2-(5-methoxycarbonyl-1,2,4-thiadiazol-3-yl)acetate (20.8 mg; 7.99×10$^{-2}$ mmol) and silver oxide (55.6 mg; 2.40×10$^{-1}$ mmol) in anhydrous dimethylformamide (210 µl) was added dropwise t-butyl bromoacetate (14.2 µl, 8.79×10$^{-2}$ mmol) under stirring at room temperature. The mixture was stirred at the same temperature for 5 hours and then the reaction mixture was directly filtered off through a layer of Celite and washed with ether.

The filtrate was combined with the washings and the mixture was concentrated. The crude syrup obtained was purified by column chromatography (1.5 g Kiesergel, hexane/ethyl acetate=1/1) to give methyl (Z)-2-t-butoxycarbonylmethyloxyimino-2-(5-methoxycarbonylamino-1,2,4-thiadiazol-3-yl)acetate (27.5 mg, yield 91.9%).

EXAMPLE 43

To a suspension of methyl (Z)-2-hydroxyimino-2-(5-methoxycarbonylamino-1,2,4-thiadiazol-3-yl)acetate (18.2 mg, 6.99×10$^{-2}$ mmol), barium oxide (53.6 mg, 3.50×10$^{-1}$ mmol) and barium hydroxide octahydrate (11.0 mg, 3.50×10$^{-2}$ mmol) in dimethylformamide (360 µl) and chloroform (180 µl) was added t-butyl bromoacetate (22.6 µl, 1.40×10$^{-1}$ mmol) under ice-cooing and stirring. The mixture was stirred at the same temperature for 1.5 hours and then pieces of dry ice were added to the reaction mixture and the insoluble matter was filtered through a layer of Celite and the residue was washed and the mixture with ether. The filtrate was combined with the washings was concentrated. The crude syrup obtained was purified by column chromatography (Kiesergel 1.5 g, hexane/ethylacetate=1/1) to give methyl (Z)-2-t-butoxycarbonylmethyoxyimino-2-(5-methoxycarbonylamino-1,2,4-thiadiazol-3-yl)acetate as white crystals (15.0 mg, yield 57.2%).

EXAMPLE 44

A suspension of isobutylyl chloride (12.13 g, 0.114 mol) and potassium thiocyanate (13.7 g, 0.13 mol) in benzene (50 ml) was heated at 80° C. for 8 hours and then 3-aminoisoxazole (2.2 g, 0.026 mol) was added dropwise thereto under ice-cooling and stirring. The mixture was stirred for 1 hour at same temperature. Then the reaction mixture was treated in the same manner as Example 15 to give methyl 2-(5-isobutylylamino-1,2,4-thiadiazol-3-yl) acetate 0.4 g.

m.p. 58°–61° C.

NMR δ(CDCl$_3$): 1.33(6H, –dd), 2.33–3.20(1H,m), 3.70 (3H,s), 3.90(2H,3), 12.80(1H,bs,NH)

IR(KBr)cm$^{-1}$: 1730, 1689.5, 1537.2, 1357.8, 1226.6.

What is claimed is:

1. A process for production of 1,2,4-thiadiazolylacetic acid compound of the formula:

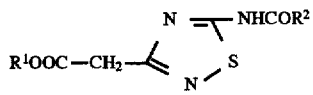

wherein $R^1$ is lower alkyl, and $R^2$ is lower alkoxy, phenoxy, benzyloxy, lower alkyl and phenyl optionally substituted by nitro or halogen, which comprises reacting an isoxazole of the formula:

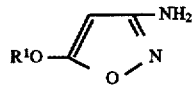

with an isothiocyanate of the formula:

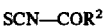

at 0°–10° C. in tetrahydrofuran or acetonitrile and subjecting to rearrangement reaction in a reaction system without any base to give the compound (II).

* * * * *